United States Patent [19]
Thielbar

[11] Patent Number: 5,824,075
[45] Date of Patent: Oct. 20, 1998

[54] CUSTOM FORMED NATURAL FIT ARTIFICIAL BREAST APPLIANCE

[76] Inventor: Janice Marie Thielbar, 48 Drakes Bay Dr., Corona Del Mar, Calif. 92625

[21] Appl. No.: 864,178

[22] Filed: May 28, 1997

Related U.S. Application Data

[63] Continuation of Ser. No. 447,793, May 23, 1995, abandoned, which is a continuation of Ser. No. 267,104, Jun. 23, 1994, abandoned.

[51] Int. Cl.⁶ ........................................................ A61F 2/12
[52] U.S. Cl. ........................ 623/7; 264/222; 264/DIG. 30
[58] Field of Search ..................... 623/7–8, 66; 264/222, 264/DIG. 30; 450/57

[56] References Cited

U.S. PATENT DOCUMENTS

| | | |
|---|---|---|
| 1,713,751 | 5/1929 | Dorogi et al. . |
| 2,543,499 | 2/1951 | Kausch . |
| 2,580,264 | 12/1951 | Wright et al. . |
| 2,633,440 | 3/1953 | Scholl . |
| 2,851,692 | 9/1958 | Livingston et al. . |
| 3,293,663 | 12/1966 | Cronin . |
| 3,301,254 | 1/1967 | Schickedanz . |
| 3,811,133 | 5/1974 | Harris ............................................. 623/7 |
| 3,911,503 | 10/1975 | Hankin ........................................... 623/7 |
| 4,086,666 | 5/1978 | Vaskys et al. ................................. 623/7 |
| 4,125,117 | 11/1978 | Lee . |
| 4,172,298 | 10/1979 | Rechemberg . |
| 4,199,825 | 4/1980 | Knoche . |
| 4,249,975 | 2/1981 | Rechenberg . |
| 4,317,241 | 3/1982 | Knoche . |
| 4,356,573 | 11/1982 | Knoche ........................................ 623/7 |
| 4,361,160 | 11/1982 | Bryce . |
| 4,401,492 | 8/1983 | Pfrommer ..................................... 623/7 |
| 4,426,742 | 1/1984 | Prahl . |
| 4,455,691 | 6/1984 | Van Aken Redinger ..................... 623/7 |
| 4,575,805 | 3/1986 | Moermann et al. . |
| 4,600,551 | 7/1986 | Erb . |
| 4,701,230 | 10/1987 | Loi ................................................ 623/7 |
| 4,787,905 | 11/1988 | Loi ................................................ 623/7 |
| 4,821,200 | 4/1989 | Oberg . |
| 4,826,501 | 5/1989 | Grundei ........................................ 623/7 |
| 5,035,758 | 7/1991 | Degler et al. . |
| 5,108,686 | 4/1992 | Griffin . |
| 5,258,036 | 11/1993 | Edenbaum et al. ........................ 623/33 |
| 5,352,307 | 10/1994 | Wild ............................................. 623/7 |
| 5,370,688 | 12/1994 | Schulz et al. ................................ 623/7 |
| 5,376,323 | 12/1994 | Eaton . |
| 5,432,703 | 7/1995 | Clynch et al. . |

FOREIGN PATENT DOCUMENTS 405154169   6/1993   Japan .......................................... 623/7

*Primary Examiner*—Mickey Yu
*Assistant Examiner*—Bruce E. Snow
*Attorney, Agent, or Firm*—Curtis L. Harrington

[57] ABSTRACT

The breast appliance and method of making of the present invention is adaptive to a variety of situations ranging from a first embodiment where impressions of both breasts of a client are available for molding, a second embodiment where a single breast is available for molding, a third embodiment where a sensitive nipple or an augmentative breast appliance is to be formed, and a fourth embodiment where breast appliances are formed from a client having neither breast available for molding.

If client's impression is made before surgery, a positive impression can be made directly from a negative mold. A molded silicone form or clay form is used to prepare a breast appliance front mold and a breast appliance back mold. Skin type nipple and breast skin silicone is first introduced into the mold before closure. After closure, a silicone gel is introduced into the cured skin silicone envelope, with removal of air and bubbles using an exit tube. After complete curing the breast appliance is removed from the mold, and worn against the surgical area with an ordinary bra, or directly onto the client's chest wall using a liquid adhesive to adhere the appliance to the body.

3 Claims, 12 Drawing Sheets

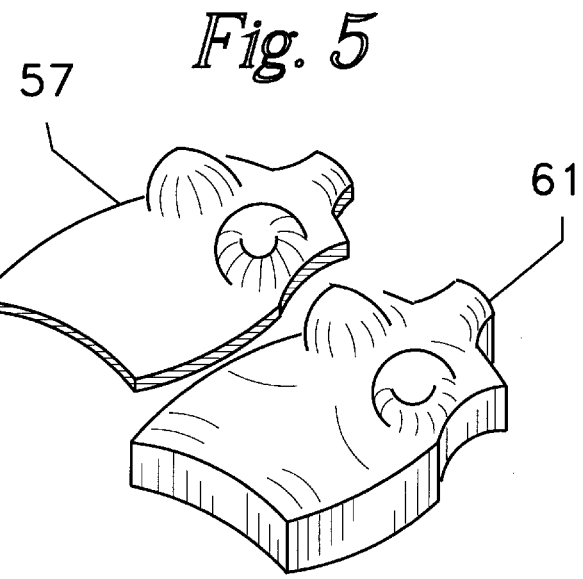
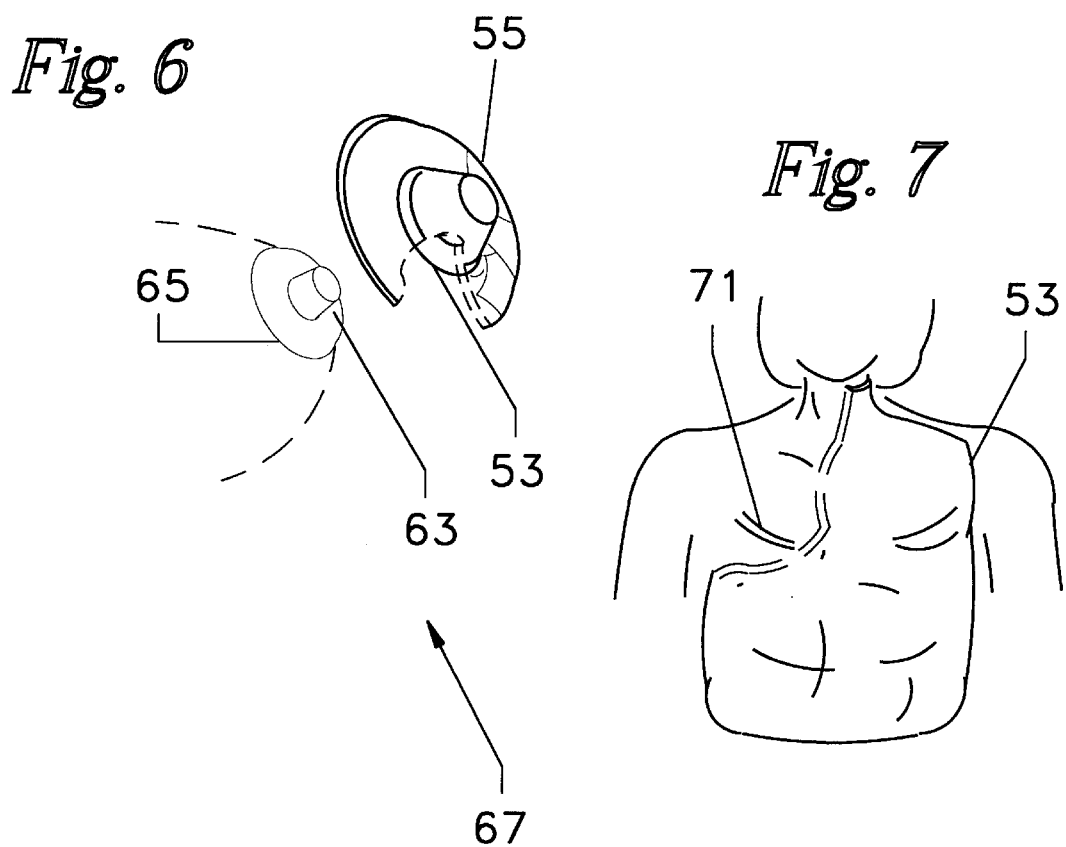

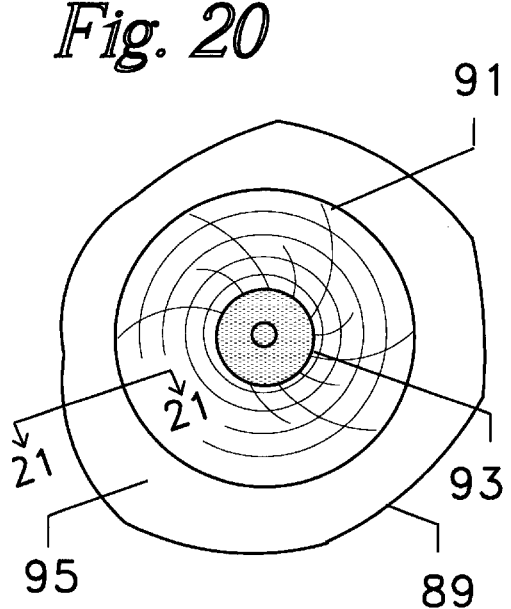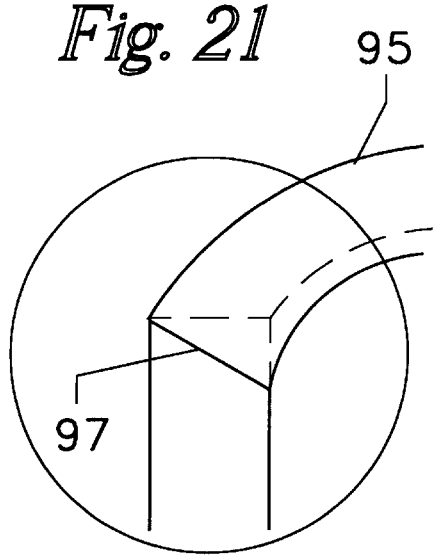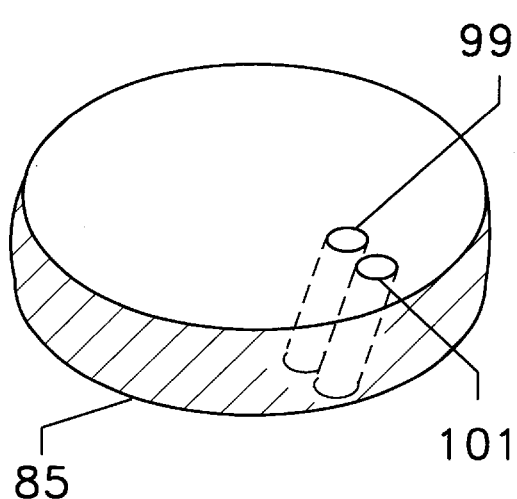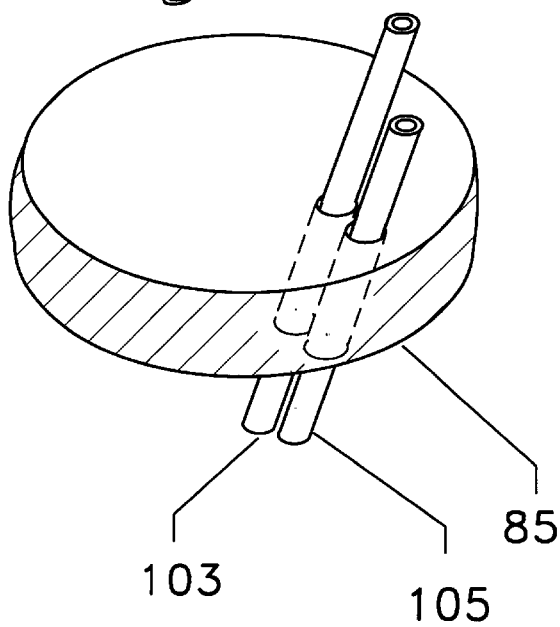

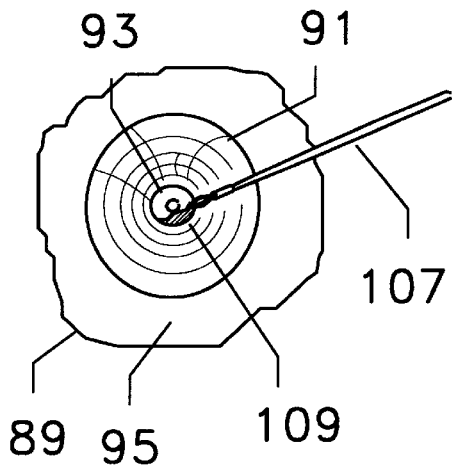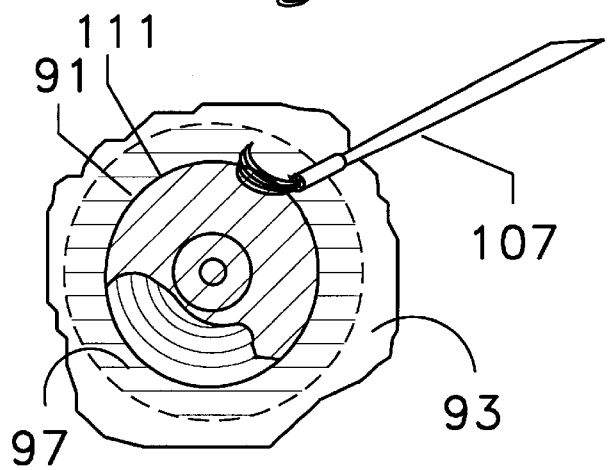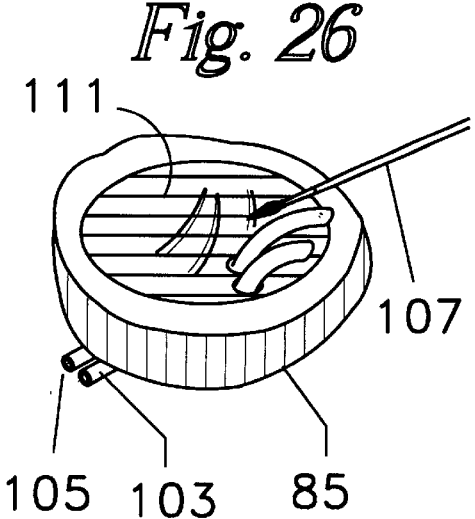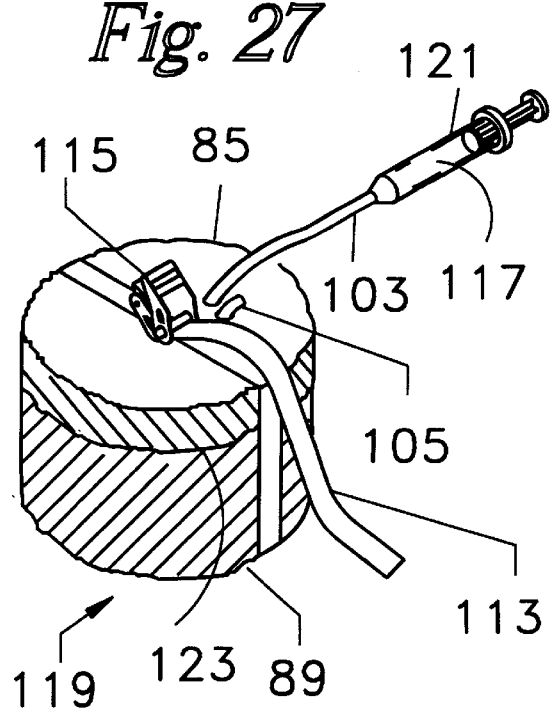

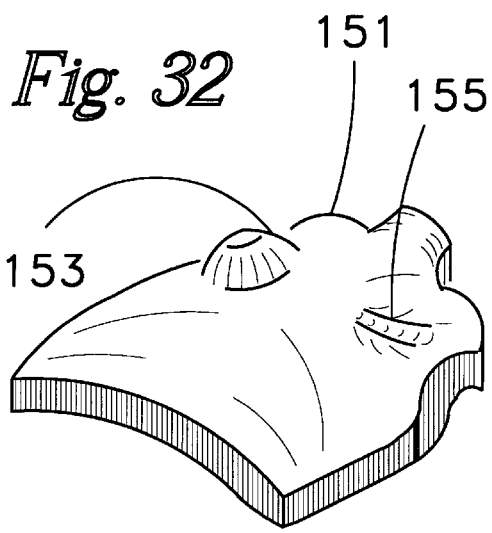
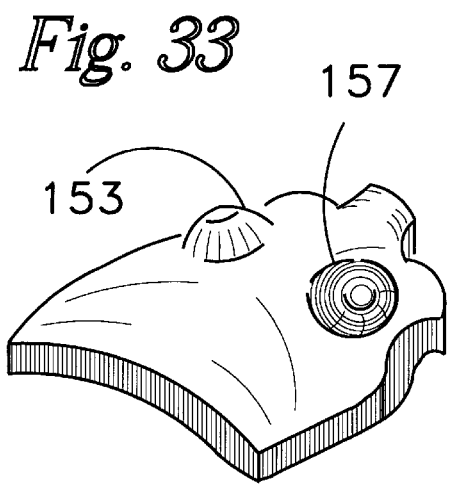
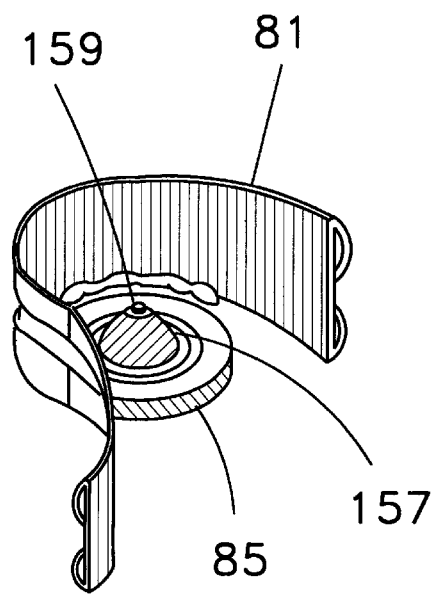
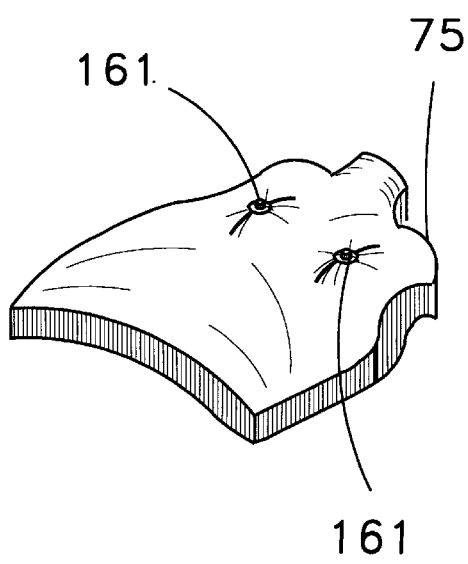

CUSTOM FORMED NATURAL FIT ARTIFICIAL BREAST APPLIANCE

This is a continuation of co-pending application Ser. No. 08/447,793 filed on May 23, 1995, now abandoned, which was a continuation of application Ser. No. 08/267,104 filed on Jun. 23, 1994, now abandoned.

FIELD OF THE INVENTION

The present invention relates to the field of external breast appliances and more particularly to a custom fitted natural external structure, known as an appliance which may be worn continuously for days, and which is most difficult to distinguish from the natural skin's surface.

BACKGROUND OF THE INVENTION

Artificial breast appliances have been employed for use over a range of time and workability. At its simplest, artificial breast appliances have taken the form of a weight of external material to be added to a bra, both for form and weight. At their most complex, artificial breast devices have been implantable, requiring a surgeon's skill and materials free from defect.

In between these two extremes, one of the most useful appliances would be one which was custom designed for the user, which could be worn naturally with or without the supportive contribution from a bra and which could be worn for several days and under the same conditions and circumstances as a natural breast. However, the prior art devices have fallen short of this goal.

For Example, U.S. Pat. No. 4,086,666 to Vaskys et al. and entitled "Breast Prosthesis," discloses a process for making an artificial breast appliance. The steps include (1) the making of a negative body cast, (2) grooving the cast to provide air circulation, (3) making a positive cast of the negative cast with fiberglass, (4) modeling the missing breast on the positive cast, (5) forming a silicone rubber mold over the sculpted missing breast and adjacent areas, (6) forming a support casting over the silicone rubber mold, (7) forming a breathing dome on the positive cast, which is much smaller than the breast to be replaced, (8) a funnel shaped opening is modeled in the dome, and diagonal cuts are formed, (9) two vinyl pads are placed on the positive cast, (10) silicone rubber is applied in thin layers to the positive cast to form a back wall, (11) colored silicone rubber is painted onto the mold supported by the support casting to simulate the coloring of the wearer, (12) woven Dacron is added to the mold, (13) the support casting is added to the positive cast, and (14) the space between the support casting and positive cast is filled. The prosthesis of Vaskys et al is removed and may be held in place with two sided adhesive surgical tape.

In U.S. Pat. No. 4,401,492, issued to Pfrommer and entitled "Breast Prosthesis and Method of Making Same," a two layer rubber skin is filled with a liquid and supported by a stiff walled backing. Here, the steps include (1) the making of a negative body cast, (2) making a positive cast of the negative cast with fiberglass, (3) sculpting the missing breast on the positive cast, (4) forming a silicone rubber mold over the sculpted missing breast and adjacent areas, even up to the shoulder and formed from "Silastic G" type silicone rubber and about one-eighth of an inch thick, (5) forming a support casting over the silicone rubber mold, (6) a retaining wall is constructed about the perimeter of the support casting, (7) once the retaining wall and volume material are joined, the cavity is filled with fiberglass reinforced resin, and (8) the formed shape is dipped in generally flesh colored silicone. Later steps include the filling with silicone gel so that the size of the artificial breast may be enlarged or reduced in size depending upon weight gains and losses of the wearer.

U.S. Pat. No. 3,811,133 issued to Eugene Harris and entitled "Weighted Prosthetic Breast" discloses a molded breast filled with resilient wadding and which is weighted from the rear of the prosthesis. Although began from the molding process, along with some clay sculpture, the molded form is cut open to stuff in the wadding.

Another method to attempt to provide an appliance is the pocket bra in which a backing cloth material is provided in a bra behind the frontal cup material, to accommodate the insertion of a plastic or other cone shaped appliance. These bras can be problematic especially if the inserted appliance is turned with respect to its fitted resting place, producing an odd-shaped appearance. Since the opening of the pocket bra must be large enough for the cone shaped appliance to fit within, the opening has presented opportunities for the appliance to slip out, particularly when the wearer bends to pick up something. Even more embarrassing, the cone shaped appliance and the bra portion holding the cone shaped appliance can, even if the wearer is bent only slightly forward, gravitationally separate from the chest of the wearer to thus expose the surgical scar tissue and the surface of the rear of the pocket bra. Further, if the bra material has weakened, the appliance may fall up to twice as far from the wearer as the wearer's other breast, and thus appear extremely unnatural.

SUMMARY OF THE INVENTION

The breast appliance of the present invention is made by first taking an impression of both breasts of a client, if possible, or the client's chest after surgery. It is preferred to have a mold of the client's breasts before surgery if possible. If client's impression is made before surgery, a positive impression can be made directly from a negative mold.

A color match is made with respect to the client's existing skin tones, breast tissue, and nipple tissue. As used herein, the term "nipple" includes the areolar skin and any skin which projects as nipple material. Skin tones may include olive dark, ruddy dark, olive light, ruddy light, transparent, and charcoal to name a few. The clay fitting is made with respect to the client's bras to determine a good fit and with respect to a balancing of weight.

Where no pre-surgical impression is available, the clients nipple from an existing breast is then measured and a nipple impression from the client's own nipple, if possible, is taken using alginate or a mixture of such materials.

A negative alginate impression is then made of the client's torso area, with plaster bandages applied to the outside of the alginate for strength and stability. A positive form is then made from the negative alginate impression. The positive form can be used in conjunction with a clay breast model and nipple form, the clay breast model shaped onto the positive form, and test fitted with the client's bra to ensure evenness and fit. Alternatively, the negative pre-surgical chest mold can be used with any material to form a mold of the client's original breast shape.

A back mold can then be made either from the positive body mold, or from another negative mold taken from the client's chest. The back mold is typically made of plaster poured against the negative mold. Then the breast form and silicone nipple is added onto the negative mold and the front mold is poured over the back mold, the breast form, and the silicone nipple mounted thereon, which will form a breast appliance mold. The breast form is removed and the inside of the breast appliance mold is finished, including a beveled interstitial area formed on the breast appliance front mold. Skin-type silicone is then applied to the inner surfaces of both halves of the breast appliance mold, the mold is closed, and silicone gel is introduced to the volume enveloped by the skin-type silicone material with the use of a fill tube extending through a drilled bore of the back mold.

Once the gel material cures, the formed breast appliance is carefully removed from the breast appliance mold.

In preparation for making the breast appliance mold, several alternatives are available. In one alternative, a clay fitting is made based upon client preferences. In another, a volume may be molded from any suitable material made in a pre-operative negative body mold.

A nipple impression may be made, if one of the client's nipples is available. Other matching techniques are available to match not only the client's skin color, but other skin characteristics including freckles, veins and internal structuring.

BRIEF DESCRIPTION OF THE DRAWINGS

The invention, its configuration, construction, and operation will be best further described in the following detailed description, taken in conjunction with the accompanying drawings in which:

FIG. 5 illustrates the removal of the negative body mold from the positive body mold;

FIG. 6 illustrates the taking of an alginate mold of the breast nipple area, separate and apart from the molds of FIGS. 1–5;

FIG. 7 illustrates a front view of a torso of the client shown in FIGS. 1–6, but after surgery and having an application of alginate applied to the torso area to take an impression of the tissue formed after surgery;

FIG. 20 illustrates a rear view, looking into the cavity formed in the breast appliance front mold once the breast form has been removed and illustrating the details which must be selectively finished to ensure a suitable finish on a resulting breast appliance;

FIG. 21 illustrates a cross sectional view of the rim of the breast appliance front mold taken through line 21—21 of FIG. 20 to illustrate the tapering surface formed in the finishing process;

FIG. 22 illustrates the drilling of a pair of holes into the breast appliance back mold;

FIG. 23 illustrates the positioning of a pair of tubes within the drilled holes illustrated in FIG. 22;

FIG. 24 illustrates the application of nipple colored silicone to the nipple portion of the breast appliance front mold;

FIG. 25 illustrates the application of breast skin colored silicone to the non-nipple portion of the breast appliance front mold;

FIG. 26 illustrates the application of breast skin colored silicone to the breast appliance back mold and surrounding the area where the tubes shown in FIG. 23 abut the scar tissue impression surface;

FIG. 27 illustrates the joining of the breast appliance back mold over the breast appliance front mold and the strap securing them together, as well as silicone filler fluid being introduced into the fill tube;

FIG. 32 illustrates an alternate procedure where only one breast is available for molding and in which the post-operative positive body mold from FIG. 10 is used as a base upon which a clay breast, with silicone nipple, is molded;

FIG. 33 illustrates the sculpting of a clay breast form upon a positive body mold;

FIG. 34 illustrates the use of the clay form of FIG. 33, mounted with silicone nipple and resting above a breast appliance back mold and readied for pouring of the breast appliance front mold;

FIG. 35 illustrates a positive body mold made from a client having sensitive post-operative nipple tissue which must be protected from rubbing and compressive contact with a breast appliance;

DETAILED DESCRIPTION OF THE PREFERRED EMBODIMENT

The description and operation of the invention will be best begun with an explanation of the three ways with which the invention hereof may be begun. In case 1, a client has available for molding either one or both of the breasts which will later be removed, and for which the formation of a breast appliance is necessary. In case 2, a client has one breast present, and desires a breast appliance to be formed over the area of the missing breast. In case 3, a client has no breast available for molding, and requires a pair of appliances derived from a personal selection of size, shape, and nipple configurations. In another case, the client requires only a nipple prosthesis.

Figure 1:
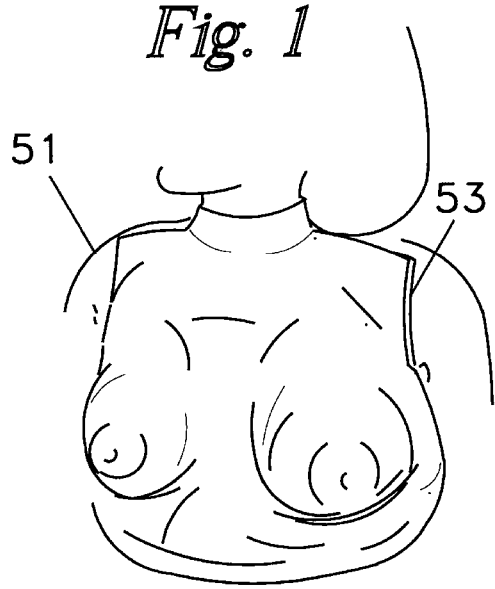
FIG. 1 is a front view of a torso of a client with both breasts present available before surgery and having an application of alginate applied to the torso area while the client's torso is in an upright position.

Referring to FIG. 1, and beginning with case 1, a client 51 with both breasts in tact before undergoing surgery is available. Many surgeries are exploratory with further surgical action occurring while the client is on the operating room table based upon laboratory results. It is therefore suggested that even potential mastectomy candidates be available for molding their chest area based upon the possibility that a mastectomy may be performed even when the client 51 is going in for a minor biopsy. If no surgery is performed, the impression of the chest area can be retained for a time and later destroyed as the client's body will after a time may no longer resemble the earlier impression.

While the client 51 is present, and either before or after the chest is molded, the client 51's skin color and nipple color is matched. Although ascertaining the client's skin and nipple color can be done by a variety of methods, one which has worked quite well is the visual matching of color simultaneous with the formation of the silicone materials which will form the breast appliance. Simple, commercially available face powder is available in a variety of colors and may be admixed with silicone to form a suspension having color and depth tones comparable with skin.

With the breast appliance to be made, three color areas need be considered. First, there is the color of the nipple. It is important that the color be matched pre-operatively to insure that longer lasting skin color changes in some clients will not cause the construction of a breast appliance which will not match after a significant time period.

The second color is the skin color of the breast exterior, and the third color is the color of the breast interior. Where veins are present, they may be simulated with lengths of fabric which will be suspended within the constructed breast appliance.

An amount of silicone starting material in excess of that which will be needed is mixed and matched against the pre-operative skin, areolar, nipple and breast tones, and then stored. Where significant amounts of a setting agent is to be used, it too can be matched and stored. The practitioner should beware the matching of color tones based upon one volume of silicone material where significant amounts of another material will be added to cause the silicone to set. This is especially true for the material to be used inside the breast appliance which will form the greater volume of the breast appliance, and whose proportion of mixing will depend on the structural consistency desired for the breast appliance ranging from firm to very soft.

In case 1, the client 51 is to have a mold made of the chest area. Preferably the mold will be made from points on the chest at least as low as a few inches below the bottom of the rib cage, to a few inches above the clavicle area, and at least as wide as halfway to the mid line extending below the arm pit area. The molding of the chest is shown in FIG. 1.

In the molding process, the shape of the breast in the standing, lying, and bra covered positions are considered. Since the breast appliance will typically be used in the standing position, its orientation when the client 51 is reclined is given preference. Further, the standing position may be modified to take to account whether the client 51 will use the appliance in a bra. This is because a client 51 with soft, but sagging breasts will elect a shape which more closely approximates the shape of the breast as would exist in a bra.

Further the client 51 can, if she is not satisfied with her natural breast shape, elect to have breast appliances made which will improve her look. However, where the client's breasts have an appearance acceptable to the client 51 in the standing position, a mold is made of the chest area.

The first step in the mold process is to obtain an alginate impression material. One such commercially available alginate impression material is sold under the trade name IDENTIC and is made by Cadco Dental Products, Inc., of Oxnard, Calif. This type of material is able to reproduce extreme surface detail. The preferred material is a dust free, five minute setting material. The five minute setting material may be somewhat more difficult to obtain, since most dental applications require a faster setting time. In taking a chest impression, several minutes may be required to apply the material, as well as to allow the material to take on the chest skin texture. A faster drying material may cause a less faithful impression or may cause the applicator to take further steps to minimize the mixing and application time.

The alginate material is in the form of a powder and is mixed with water. Varying the amount of water enables the applicator to vary the viscosity and thickness of material being applied to the client's chest area. The recommended amount of water for one type of alginate has been 16.0 cc of water per 6.0 grams of dry alginate powder.

Once a sufficient amount of alginate has been prepared with warm water, an alginate layer 53 is applied to the client 51's chest while the client 51 is preferably in a standing position. In standing position, the breasts take on the most desirable orientation. If the client 51 wishes modifications, or even several sets of different breast appliances with different orientations, such may be formed later, after surgery, in addition to the impressions taken at this early stage.

The alginate sets in five to ten minutes. However, because the alginate is present in a relatively large mass with a relatively small thickness of from one fourth to one half of an inch across the client's chest, more structural support is needed to both remove and handle the alginate negative case which is formed of the client's chest.

Figure 2:
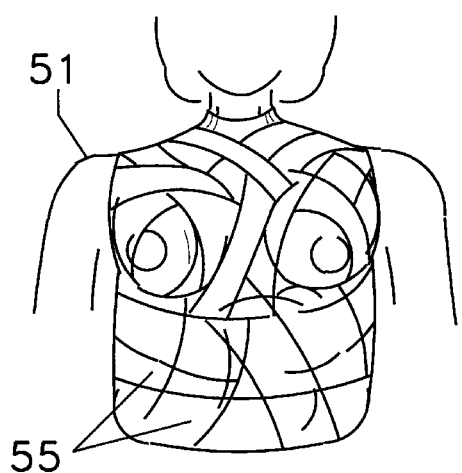
FIG. 2 is a front view of a torso of a client after the alginate shown applied in FIG. 1 is set, and illustrating plaster bandages applied over the alginate set to give greater structural strength to the torso impression and to form a negative mold.

For this additional support, plaster bandages 55 are applied to the external surface of the cured alginate layer 53, as is shown in FIG. 2. Plaster bandages 55 are loosely woven gauze strips which are available impregnated with plaster. All that need be done is to dip the plaster bandage roll into a supply of warm water, squeeze out the excess water, and apply directly to the alginate material in a crossing pattern. A triple application of the triple crossing pattern is recommended for strength. Setting time for the plaster bandage may range from two to eight minutes. A further supply of plaster may, if necessary, be smeared over the plaster bandages 55 to form a more reinforced mass, perhaps followed by further application of plaster bandages 55. Such a technique may be necessary where there is not enough plaster in the plaster bandages 55.

Figure 3:
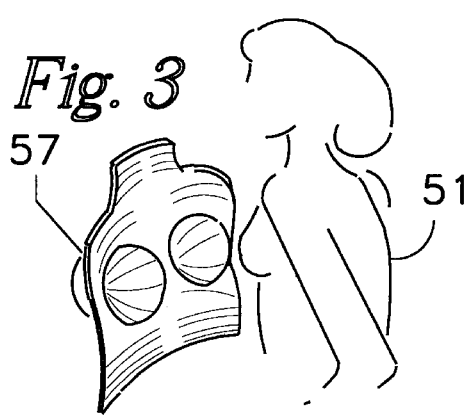
FIG. 3 is an illustration of the removal of the negative mold formed in FIGS. 1 and 2 being removed from the client.

Also consider the use of a refrigerator or other method to cool the bandages to reduce the any shrinkage which may occur. Once the plaster bandages 55 have dried and hardened, a negative mold 57 of the client 51's chest is formed and is removed gently from the client 51, as is shown in FIG. 3. Next, a positive body mold is formed by pouring a plaster mixture 59 into the negative mold 57. Once the plaster dries and hardens, it becomes positive body mold 61, and the negative mold 57 is removed from around it as is shown in FIG. 5. A chest sized positive body mold 61 is important because it has sufficient mass and structural integrity to enable further work and will not easily break.

As will be explained, the molds from which the breast appliance is formed will be neither the negative mold 57 nor the positive body mold 61. This is so for several reasons. First, if wither of the two molds 57 or 61 were damaged in formation of the breast appliance (to be shown), which formation always occurs after surgical breast removal, the impression would be lost. Secondly, handling the relatively larger molds to make a relatively small breast appliance would be unduly bulky and onerous. Third, the sealing pressure needed to be exerted between the halves of the mold which form the breast would come close to breaking the larger molds. Fourthly, and as will be shown, some material in the negative breast mold will need to be removed to provide a thin tapering area of silicone which will be used to "blend" in with the skin of the client 51.

Therefore, although a negative breast mold is formed as a part of the negative mold 57, a further negative breast mold will be formed, as will be shown later. In accord with other cases in addition to case 1, a separate alginate mold may be taken of the client 51's nipples. This may be particularly the case where the client 51's nipples are formed of an unusual shape or having an extended center portion. This step can also be used in a case where an implant is elected after a mastectomy, and a nipple alone may be made to adhesively fit over the tissue in which the implant is placed. Especially in the case where an implant might be elected, a separate nipple mold needs to be made.

A separate nipple mold can be made with reference to FIG. 6 by applying the alginate material in a suitable layer 53 to the client 51's nipple 63, and an inch of additional diameter beyond the client 51's areolar 65. There may or may not be a small section of plaster bandage 55 applied to the outer surface of the alginate to add support and help to retain the surface contour of the breast immediately about the nipple area. Typically, a silicone nipple can then be formed directly by brushing appropriately colored silicone, with its setting agent into a nipple mold 67 formed by the procedure shown in FIG. 6. The details for forming the nipple material will be described at further length below.

Once the client 51 has participated in the above procedures, a surgery is typically performed which may leave the client 51 in one of several states. A large portion of one or both of the client 51's breasts may have been removed. The procedures vary widely, and the results can vary. One procedure may include the total removal of all nipple tissue and all breast tissue, typically leaving a laterally extending scar layer on the chest tissue. Another procedure may result in removal of the bulk of the breast material, but leaving the nipple in tact. In another case additional intertissue of excessable amount may be present. In this case, the client's nipple 63 may be very sensitive, not just after the surgery, but permanently.

In another case, some breast material may be present, both in terms of a particularized size and shape. For example, a radial half of the breast may be removed leaving a smaller portion of the other half. In another example, one or more folds of tissue may be left in an unattractive or difficult configuration. Regardless of what shape and amount of tissue remains on a client 51's chest, the method described herein will take account of it in forming the breast appliance of the present invention.

After the client 51 surgery, and the passage of a sufficient amount of time for any swelling or inflammation to subside, a mold of the client 51 chest is made. It is important not to make the mold too soon, before healing is completed, since further healing after a mold is made will reduce the fit of the breast appliance against the client 51 chest.

Figure 4:
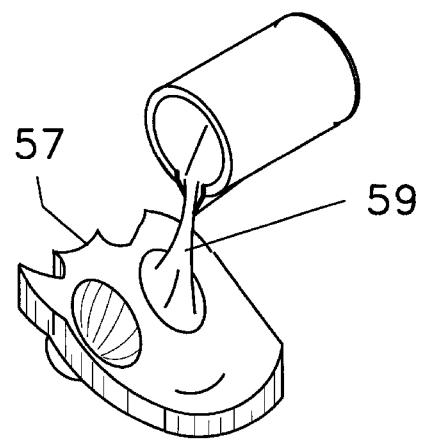
FIG. 4 illustrates the pouring of plaster into the negative mold shown in FIGS. 1–3 to form a plaster positive body mold.
Figure 8:
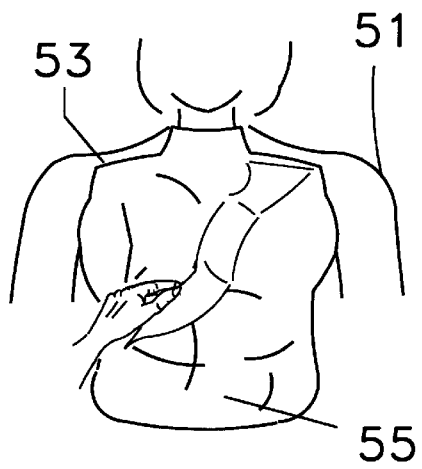
FIG. 8 is a front view of a torso of a client after the alginate shown applied in FIG. 7 is set, and illustrating plaster bandages applied over the alginate set to give greater structural strength to the post-operative torso impression and to form a post-operative negative mold.
Figure 9:
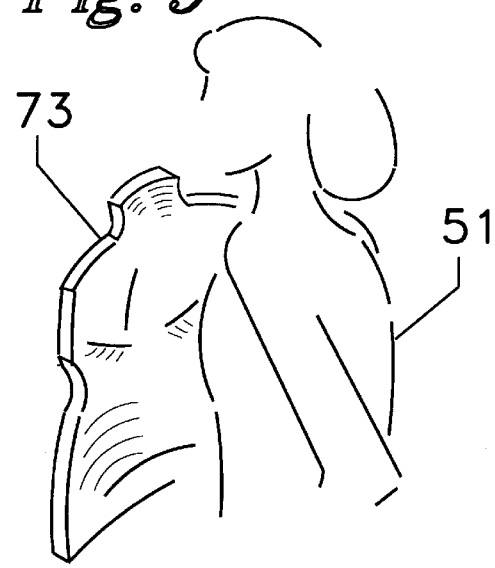
FIG. 9 is an illustration of the removal of the post-operative negative mold formed in FIGS. 7 and 8 being removed from the client.

As can be seen in FIGS. 7–9, the client 51 as she appears post-surgery which resulted in a double mastectomy. There is scar tissue 71, and the alginate layer 53 is being laid over this scar material in a manner identical to that shown in FIGS. 1–3, to form a post operative negative body mold 73, as shown in FIG. 7–9. From the post operative negative mold 73, a post operative positive body mold 75 is formed, similar to the procedure shown in FIGS. 4 and 5. It is the post operative body mold 75 which will serve as the basis for the rear wall of the breast appliance of the present invention, as will be shown.

As previously mentioned, a smaller mass of material need be formed to act as mold for the breast appliance of the present invention, for and ease of size. Beginning with the post operative body mold 75, and referring to FIG. 11, a smaller amount of alginate layer 77 is spread over one of the right and left scar areas of post operative body mold 75. Enough of the smaller amount of alginate layer 77 is spread beyond the base of the outline of the previously present breast to insure that enough of the surrounding material will be cast from which a tapering edge can be formed.

Figure 11:
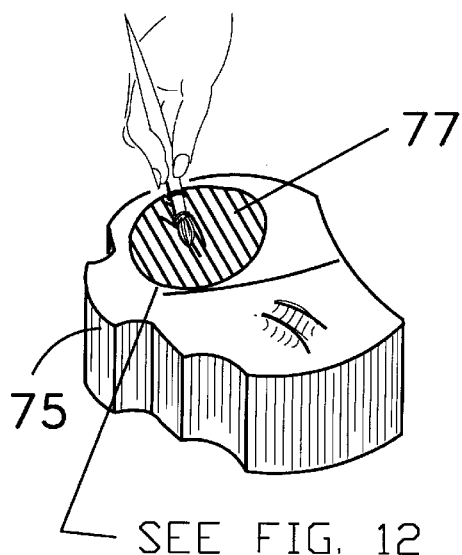
FIG. 11 illustrates an alginate impression being taken with respect to a single breast area of the post-operative positive body mold shown in FIG. 10.
Figure 12:
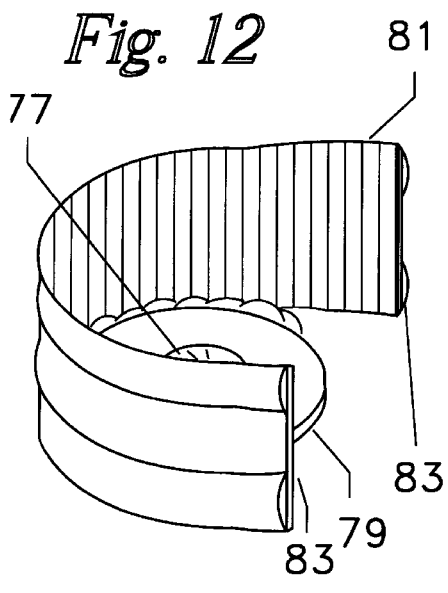
FIG. 12 illustrates the surrounding of the smaller alginate impression taken in FIG. 11 with a sealable barrier before plaster is poured onto the smaller alginate impression to form a breast appliance back mold.

After it has cured, the smaller alginate layer 77 may have plaster placed against its outside to form a stronger structural form. In any event, smaller alginate layer 77 is then gently lifted from the post operative body mold 75, as is shown in FIG. 11, and placed on a flat surface, shown in FIG. 12. The side of the smaller alginate layer 77 which faced the scar tissue of the post operative body mold 75 is placed upwardly with regard to a flat surface 79. Flat surface 79 may be moveable, or it may be a table top.

Next, a flexible barrier 81 is formed into an annular cylinder and further formed to closely surround the smaller alginate layer 77, making sure that the shape of the smaller alginate layer 77 is preserved in all three directions. The end edges 83 are attached abutting one another to form a leak proof annular cylinder. The cylinder shape formed by the flexible barrier 81 may deviate from circularity as necessary to closely conform to the edge of the smaller alginate layer 77. The space between the end edges 83 and the space between the flexible barrier 81 and the flat surface 79 may be sealed with putty or clay, or any other disposable or workable material.

It is understood that the smaller alginate layer 77 could have been taken directly from the client 51 without the need to form a positive body mold 75. However, the positive body mold 75 has advantages of enabling reference points, enabling measurement with a bra and generally visualizing the appearance which the client 51 is trying to achieve. Also, the formation of a positive body mold 75 will eliminate the need to take a smaller alginate mold of the portion of the client's chest where the breast appliance is to be located. This procedure can help to minimize client time and discomfort in that it brings to a minimum the client 51's mold activity.

Next, a volume of plaster is poured into the area inside the flexible barrier 81 to form a shape approximating a cylinder whose operative surface abutting the smaller alginate layer 77 will be an exact replica of the client 51's post operative tissue, as well as the post operative tissue area of the post operative body mold 75.

Figure 13:
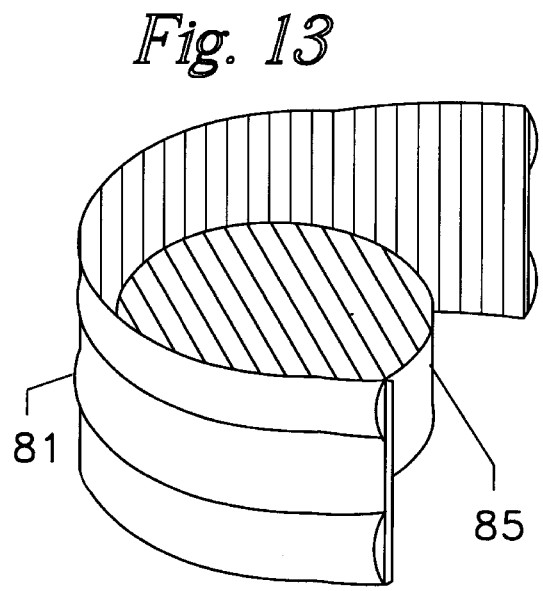
FIG. 13 illustrates the removal of the sealable barrier exposing the breast appliance back mold.

Once the plaster has hardened to form a breast appliance back mold 85, as is shown in FIG. 13, the flexible barrier 81 is removed, and the back mold 85 is inverted, and the smaller alginate layer 77 is removed. The breast appliance back mold 85 is a negative mold of a surface which should abut the client 51's post operative chest area.

Next, a breast impression needs to be made from the negative mold 57. Care is made in selecting the material to be molded into the negative body mold 57 to ensure that it captures the nipple detail of the client 51. A mold release is typically sprayed into the appropriate breast cavity of the negative mold 57 to ensure that the mass placed therein will adequately capture the details of the pre-operative breast form.

Suitable releasing agents include soaps, stearic acid and kerosene, petroleum jelly, and spirits of camphor. It should be pointed out that a suitable releasing agent should be one which will not contaminate the silicone. One such material which can be employed as a releasing agent is a spray lacquer. One such lacquer is sold under the name ZYNOLYTE and is commercially available from Compton, Calif.

Figure 15:
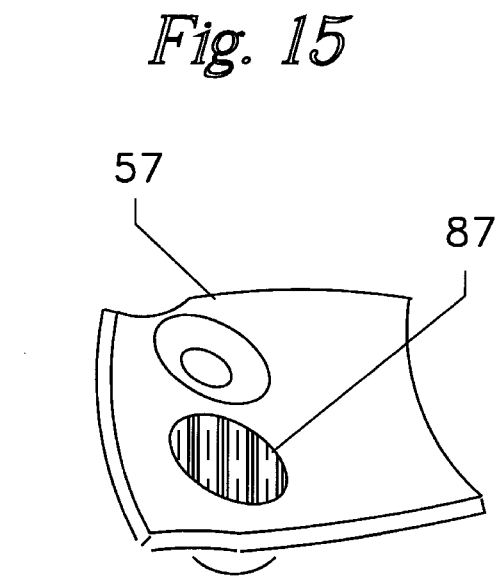
FIG. 15 illustrates the rear side of the pre-operative negative body mold and the formation of a positive breast form impression therewith.
Figure 16:
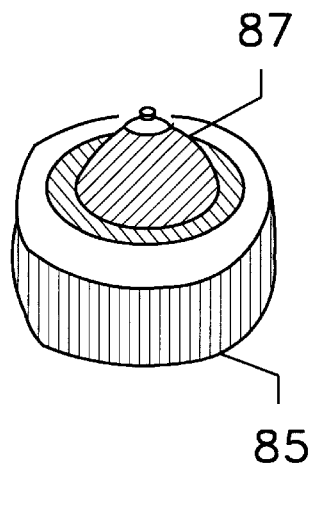
FIG. 16 illustrates the positive breast form being mounted atop the breast appliance back mold.

Once a breast form 87 is molded from a firm silicone and removed from the breast cavity of the negative mold 53, as shown in FIG. 15, it is placed atop the breast appliance back mold 85, as is shown in FIG. 16. The interface between the scar tissue surface of the breast appliance back mold 85 and the back side of the breast form 87 will not and is not expected to match exactly. However, both the support and height of the breast form 87 must be therefore taken to account to insure that breast form 87 sits properly atop the breast appliance back mold 85.

Figure 17:
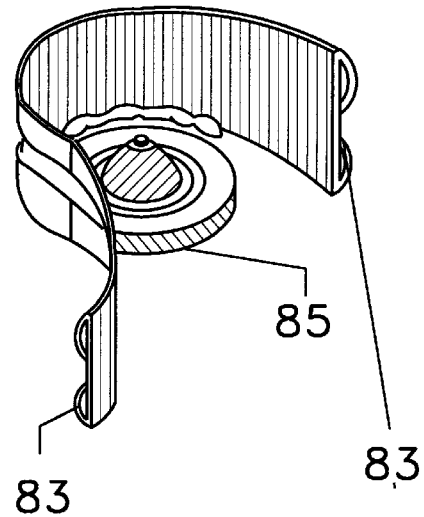
FIG. 17 illustrates the configuration of FIG. 16 being surrounded by a sealable barrier of a height sufficiently greater than the breast form while mounted atop the breast appliance back mold.

Referring to FIG. 17, the flexible barrier 81 is again brought around the breast appliance back mold 85. Additional sealing may be accomplished between the upper surface of the breast appliance back mold 85 and the flexible barrier 81, but care must be taken to make sure that this is minimal and that any clay or putty sealer not touch any of the surface of the breast appliance back mold 85 which carries the client 51's impression. In addition, the edges and surfaces of the breast appliance back mold 85 are treated with a release agent to make sure that neither of the breast form 87 or the subsequently added plaster will stick to it.

Figure 18:
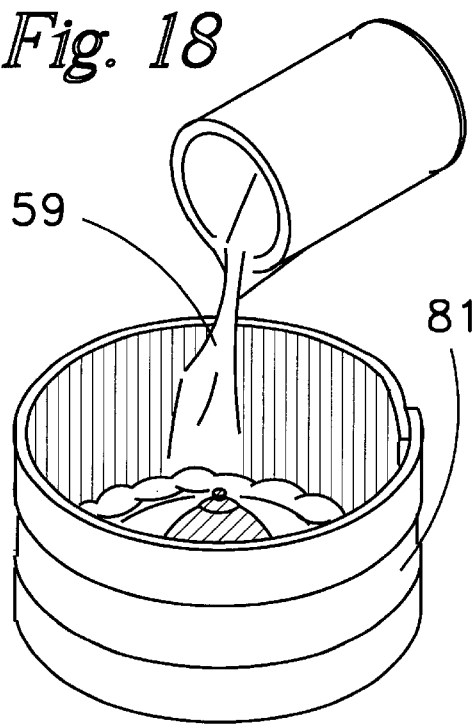
FIG. 18 illustrates the pouring of plaster into the structure shown in FIG. 17, the upper layer of plaster to form a breast appliance front mold.

Referring to FIG. 18, an amount of additional plaster mixture 59 is poured into the sealed flexible barrier 81 and over the breast form 87, totally covering it, and with sufficient additional plaster to insure the structural integrity of what will become breast appliance front mold 89 when the plaster shown being poured in FIG. 18 hardens and dries.

Figure 19:
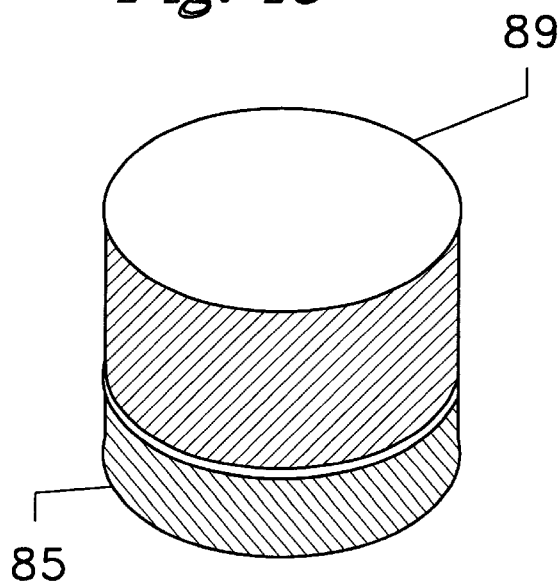
FIG. 19 illustrates the structure shown in FIG. 18 once the upper layer of plaster has set, and the sealable barrier has been removed.

FIG. 19 illustrates the breast appliance front mold 89 overlying the breast appliance back mold 85 with the flexible barrier 81 removed. The breast appliance front mold 89 is then gently separated from the breast appliance back mold 85, and the breast form 87 is then gently removed from the breast appliance front mold 89.

The next step will determine the surface finish of the breast appliance (still yet to be shown). Referring to FIG. 20, the breast appliance front mold 89 is shown lying on its side, looking into the void which was previously occupied by the breast form 87. The inner surface, not including the nipple area, referred to as the breast mold surface area 91 may be pitted and rough. A hand sanding operation is initiated with sand paper ranging from coarse to a successively finer grain. In some instances where there are pits on the surface to be smoothed, such pits may be filled in with small amount of plaster swiped across the pit, and sanded down after drying and setting.

Care must be taken not to sand the nipple mold area, shown in FIG. 20 with the numeral 93, as it is not intended to be smooth. If there are any gross defects or anomalies with respect to the nipple, they must be worked carefully with tools with a mind toward preserving the texture and form of the nipple. Once the nipple mold area 93 and breast mold area 91 surfaces of the breast appliance front mold 89 is carefully prepared, an amount of the breast appliance front mold 89 immediately surrounding the breast surface outer edge of the mold is to be removed.

This rim area 95 will be removed by removing slightly more material immediately adjacent the breast mold area 91 and removing only a very small amount of material immediately adjacent the outer cylindrical surface of breast appliance front mold 89. Remembering that the rim area 95, as originally formed, was an exact match with the opposing surface of the breast appliance back mold 85, a removal of material, particularly a larger removal of material nearer the concentrically inner edge of the rim area 95 will enable any material placed between the breast appliance front mold 89 and breast appliance back mold 85 to be formed into a taper leading concentrically outwardly away from the center.

A detail of the removed material is illustrated in FIG. 21, with the area which would otherwise be occupied by the material which was removed shown in phantom. The remaining surface is a beveled surface 97.

Next, and referring to FIG. 22, a pair of closely spaced holes 99 and 101 are drilled completely through the breast appliance back mold 85. These holes are positioned nearest the portion of breast appliance back mold 85 which would correspond to the chest area nearest a vertical line extending from the pit of the arm. This corresponds to a surface of the portion of the breast appliance back mold 85 which is lower than most of its other surface. If the breast appliance back mold 85 were inverted, it would represent a higher fill area, and this is the reason for the positioning of the holes.

A pair of tubes 103 and 105 are positioned in holes 99 and 101, as is shown in FIG. 23. The tube 103, which will be utilized for filling the assembled breast appliance mold with filler material extends about one half to one inch above the surface of the breast appliance back mold 85 while the tube 104, which will carry displacement air, rises only slightly above the surface of the breast appliance back mold 85. The lengths of the tubes 103 and 104 will preferably, on the other side of the breast appliance back mold 85 extend to a length of from ten to twelve inches. Preferably the breast appliance back mold 85 is checked for fit against the breast appliance front mold 89.

Next begins the steps for actual construction of the breast appliance. The colors which were matched using liquid silicone to which face powder was added to achieve such color are retrieved from storage. Referring to FIG. 24, the inner surface of the breast appliance front mold 89 is sprayed with a release agent, with care being taken that it does not unduly run or collect to one side. The breast appliance front mold 89 may be inverted to ensure that the release agent does not collect, and if an excess is present it will run toward the base rim. The release agent may be carefully brushed into the nipple mold area 93 to ensure that nipple details are not obscured.

Once the release agent has been sprayed into the mold, the nipple silicone material is mixed with its setting agent, and it is painted into the nipple mold area 93. The nipple silicone material must be fully wetted and applied to the nipple mold area 93. In some cases an air bubble (to be shown later) may be deliberately formed behind the smallest portion of the nipple to provide a more natural feel to the finally formed breast appliance, since a small bubble of entrapped air can compress and spring back in a manner more closely approximating that of a natural breast. Alternatively, the volume of the extended portion of the nipple can be left open to be filled with the same gel which will fill the formed breast appliance. The structural integrity of the nipple can be particularly important for interaction of the breast appliance with clothing. The nipple tip end would have enough structural strength to manifest a natural look with sheer clothing, but would not express its shape through a more tightly worn bra. The same air bubble may be employed in forming a separate nipple (as will be shown).

Referring to FIG. 24, a paint brush 107 is shown employed for adding nipple silicone material 109. A brush 107 may be used to ensure that the material is thoroughly spread into each tiny texture structure of the nipple mold area 93. One such nipple silicone material 109 is sold under the trade name FACTOR II, from Lakeside, Ariz. Another material is available commercially from Nusil Technology under the designation CF16-2186, FACTOR II. Like most silicones, it is commercially available as a volume of part "A" and a volume of part "B", which can be subsequently mixed to initiating setting. These components are also known as "base" and "catalyst." The consistency of the material after setting up will depend upon the proportions of the "A" and "B" materials selected.

Since a color match with just the "A" material will be diluted if the "B" material is added in an uncolored state, the color match may be accomplished with respect to both volumes before those volumes are mixed together. Alternatively, the color match for part "A" may be made a shade darker to take account of the part "B" which will be added to catalyze part "A," in addition to colored earth pigments and face powders.

In addition to the addition of face powders, an amount of kaolin is added to "fill" in the areas which will be colored by the face powder and add to the opaque, skin-like appearance. For nipples, typically 100 grams of the 2186 silicone base (part "A") is mixed with two teaspoons of kaolin. The 100 gram mix is then divided into 5 and 10 gram amounts. A given 10 gram container can then be used to match the nipple color of the client 51. It is recommended that the part "B" or catalyst be added in a ratio of ten parts of base "A" to one part of catalyst "B." The nipple silicone 2186 material should not be catalyzed until immediately before use. It is preferred to draw a vacuum on the catalyzed mixture to ensure that all bubbles are removed from the mixture. Bubbles can spoil the consistency and texture of the nipple area formed on the breast appliance. Vacuum de-airation at 28 inches of Mercury is recommended while holding the vacuum for 3 to 5 minutes. Once mixed, the pot time is from 10 to 20 minutes depending upon room temperature. The total cure time is from 4 to 6 hours, and again room temperature is a factor.

The silicone (CF16) 2186 material is left to set in the nipple mold area 93 for 3 to 4 hours. It is important to allow the nipple silicone 2196 material to completely set so that the coloration between the skin of the breast appliance being formed and the breast appliance nipple material will not intermix, obscuring the line of separation. The nipple formed will typically require about 2.5 grams of material. As such, some of the color matched nipple silicone 2186 material may be held back in case the breast appliance needs to be re-molded, or to have another application applied.

It is also at this time that a nipple structural air pocket can be formed. An air bubble left in the outermost projecting portion of the nipple will provide a more gentle structural projection for the tip end of the nipple from the breast appliance which more accurately simulates a natural nipple. In sheer clothes the nipple on the breast appliance will more readily express its shape and presence, while in more restrictive clothes its expression will diminish. Without the nipple structural air pocket, the expression of the tip of the nipple from the breast appliance will be of greater magnitude even in restrictive clothing, and will have a natural touch through the clothing. Further, the presence of the nipple structural air pocket will more accurately simulate a natural breast and nipple to the touch through the clothing. This nth degree of detail is often necessary for the complete confidence of the client 51 in a breast appliance which will eliminate worry and undue attention to a breast appliance.

The nipple structural air pocket can be formed by first forming a flat round plate of nipple silicone material 109 and allowing it to cure sufficient for a minimum amount of structural strength. Once the nipple mold area 93 is painted in with the nipple silicone material 109, the flat round plate of nipple silicone is placed to cover the lowermost "bore" which is the negative impression of the outermost portion of the nipple. The back of the flat round plate may be painted over with further amounts of nipple silicone material 109 to ensure that the nipple structural air pocket will be closed and not in fluid air communication with the silicone which will occupy the bulk of the breast appliance.

The nipple silicone 2186 material may be applied in a layer as thick as needed, and may be from one eighth to one fourth of an inch thick. The nipple silicone 2186 may also be air brushed into the nipple mold area 93 if sufficient equipment is available, as well as a structure to block any stray migration of nipple silicone material 109 onto other areas. Once the nipple silicone 2186 material is completely cured, the silicone for the "skin" of the breast appliance is applied. The silicone material is also silicone 2186, and is also formed in a 10:1 ratio, as was the case for the nipple material.

The weight of 2186 silicone material is dependent upon the size of the breast appliance since a larger breast appliance will require more surface area. In addition, a larger breast appliance will require a thicker skin to adequately support the mass of silicone gel inside it. For a breast appliance corresponding to a bra cup in the range of "size A," to "size B," about 40 grams of the 2186 silicone material is required. For a breast appliance corresponding to a bra cup in the range of "size B," to "size C," about 60 grams of the 2186 silicone material is required. For a breast appliance corresponding to a bra cup in the range of "size C," to "size D," about 80 grams of the 2186 silicone material is required.

For extra-large breast appliance sizes, an additional 40 grams will be required to form the surface area of an inside "Pocket," or air space. In the larger sizes, the "pocket" is used to lessen the weight of the breast appliance, particularly where both breasts are being replaced.

Again, the 2186 silicone material may be air brushed, painted or otherwise sprayed into the breast appliance front mold, as is shown in FIG. 25 where it is shown being applied with a brush. The skin silicone material 111 is shown as being partially painted in, and it covers the nipple silicone material 109. Both the nipple silicone material 109 and the skin silicone material 111 may be referred to collectively as tissue silicone material. The tissue silicone material, as has been shown, differs only in the amount and color of pigment added, and spatial location of the tissue silicone material within the breast appliance front mold 89 and breast appliance back mold 85. It is important to achieve an even depth of the skin material. There are many ways to manipulate the skin material, but it must be remembered that once the catalyst is mixed in, the skin will begin to set in minutes.

One material which facilitates the workability of the silicone skin material 111 is a product known as "200 fluid, 100 CST," which is commercially available from Dow Corning. This material is applied to the hands before physically manipulating the silicone skin material 111 to prevent such skin material 111 from pulling away from the breast appliance front mold 89.

In addition to the breast mold surface area 91 within the breast appliance front mold 89, a thin layer of skin silicone material 111 is applied to the rim area 95, making sure that it is continuous with the skin material 111 of the breast mold surface area 91. The edge where the rim area 95 meets the breast mold surface area 91 will likely form the thickest dimension of the skin silicone material 111. This will aid in retention of shape.

Remembering that the rim area 95 is tapered, the closing of the breast appliance back mold 85 which is not tapered will cause the skin silicone material 111 to be squeezed thin in the direction concentrically outward with respect to the rim area 95. Of course, for a given degree of taper, both the breast appliance back mold and the breast appliance front mold 89 could contain rims whose composite taper would add to the total amount of taper needed. However, since the client 51's chest will be flat in the area surrounding the breast removal area, it is preferred that the breast appliance front mold contain the tapering rim area 95.

Referring to FIG. 26, and a soon as possible after the skin silicone material 111 is applied to the breast appliance front mold 89, the skin silicone material 111 is applied to the impression side of the breast appliance back mold 85. The material 111 is applied over the whole surface, remembering that any excess will be squeezed concentrically inwardly, and somewhat concentrically outwardly with respect to the rim area 95.

Special care is taken to make certain that the area of the breast appliance back mold 85 immediately adjacent the tubes 103 and 105 is completely wetted with the skin silicone material 111. Otherwise, some of the silicone gel which will be added could seep between the skin silicone material and the breast appliance back mold 85.

As soon as practically possible, and once the layer of skin silicone material 111 is properly applied to the inside of both the breast appliance back mold 85 and the breast appliance front mold 89, the molds are brought back into mating alignment in the same position and orientation as they were when previously shown in FIG. 19. The alignment may be marked as in the step of FIG. 19 before the breast appliance back mold 85 is separated from the breast appliance front mold 89, to aid in re-alignment. Alignment is important not only because the breast appliance to be formed is gravitationally oriented, but because the gravitational orientation must match the chest tissue orientation of the client 51.

Once the breast appliance back mold 85 and the breast appliance front mold 89 are joined, it is preferable to secure them with a strap 113, the strap 113 being fixably tensioned with a buckle 115. Note FIG. 27, and the position of the breast appliance back mold 85 with respect to the breast appliance front mold 89. This is the position which is most advantageous in filling the breast appliance with silicone gel.

The silicone gel used, like the nipple and skin silicone material 109 and 111, may be of any type, but it is recommended to use SYLGARD brand 527 primerless silicone dielectric gel which is commercially available from Dow Corning. The silicone gel, hereafter referred to as gel 117 is a self healing gel, and also has a two part, "A" and "B" liquid. However, it is recommended to vary the amounts of each part to achieve a variety of structural consistencies. Although the manufacturer recommends a 1:1 ratio for a self healing resilient gel-like mass, other consistencies may be sought.

Since the client 51 will normally try to match the previous breast consistency, the consistency of the breast appliance will need to be similarly varied. This is particularly necessary where a younger client 51 desires a more rigid consistency matching an overall firm body tone, and where an older client would require a much less rigid consistency to match a softer body tone.

A softer tone is achieved by adding less of the "B" component. For example, one preferred softer formulation involves the use of 330 grams of "A" and 270 grams of "B." The firmest combination would involve equal amounts of "A" and "B." Remember that the total volume of the mixture will depend upon the size of the breast appliance to be produced. In addition, it is preferable to make more of the gel 117, since any shortage would have to be made up by re-mixing a batch which would not cure evenly with the first amounts introduced into what is now the breast appliance mold 119, formed by the joining of the breast appliance front mold 89 and the breast appliance back mold 85.

Further, by allowing the silicone gel 117 to cure within the envelope of the silicone tissue material, the gel is at least partially cured to the silicone tissue material. The silicone gel 117 significantly strongly adheres to the silicone tissue material. This is advantageous in that the silicone tissue material and the silicone gel 117 material then form additional bonds which further support and strengthen the resulting structure. Further, the silicone gel 117 material will cure to a shape defined by the silicone tissue material, and together they will resiliently hold their shape. This definitely prevents the cured gel 117 shape from turning within the silicone tissue material envelope.

The mixed gel 117 is loaded into a syringe 121 and is forced through tube 103 and into the breast appliance mold 119. Size of the syringe 121, and size of the cavity within the breast appliance mold 119 will determine how many times the syringe 121 will be re-loaded before the breast appliance mold 119 is filled. Once the breast appliance mold 119 is filled, the gel 117 and bubbles will begin to emerge from the tube 105. The breast appliance mold 119 should continue to be filled with the syringe 121 until the stream of liquid from the tube 105 emerges as a bubble free stream.

The breast appliance mold may be tilted and shaken to free any entrapped bubbles, in order to get them to come to the surface and exit through the tube 105. Once the breast appliance mold 119 is filled and free of air, the tubes 103 and 105 are clamped to seal them, and thereby prevent any air or flow of gel 117 into or out of the breast appliance mold 119. The syringe 121 will typically be removed and all gel 117 removed to ease in cleaning and to keep the syringe 121 free of obstruction for the filling of the next breast appliance mold 119. The filled breast appliance mold 119 is then left to stand, so that the setting of the gel 117 will be completed. Preferably, it will be left to stand for eight to ten hours, especially if such time is available.

For the larger sized breast appliances, a longer cure time, perhaps over a weekend is encouraged to make sure that curing is complete. It should also be remembered that a larger sized breast appliance may require a greater degree of firmness to compensate for the larger size. A firmer breast appliance, but having more mass, will react to forces in a manner similar to a smaller sized breast appliance of lesser firmness.

Once the requisite time has passed for setting to occur, the tubes 103 and 105 extending from the breast appliance mold 119 are removed, usually by wedging the seem between them, and once pried partially open by grasping them and pulling them from the breast appliance back mold 85. The breast appliance mold 119 is opened carefully, usually by carefully wedging a seem 123 dividing the breast appliance back mold 85 and the breast appliance front mold 89. A prying instrument may be used to separate the breast appliance mold 119.

Remember that the separation involves the parting of plaster material from the skin silicone material 111, and that the integrity of this material is of paramount importance during separation of the breast appliance mold 119. Further, and of even greater importance, the mold 119 must be opened carefully and in a manner that the breast appliance back mold 85 separates from the breast appliance. This should happen naturally since the mold area of the breast appliance back mold 85 is flat and will usually offer the least resistance, while the breast appliance front mold has a larger surface area which is both parallel and perpendicular to the direction of separation of the mold 119.

Figure 28:
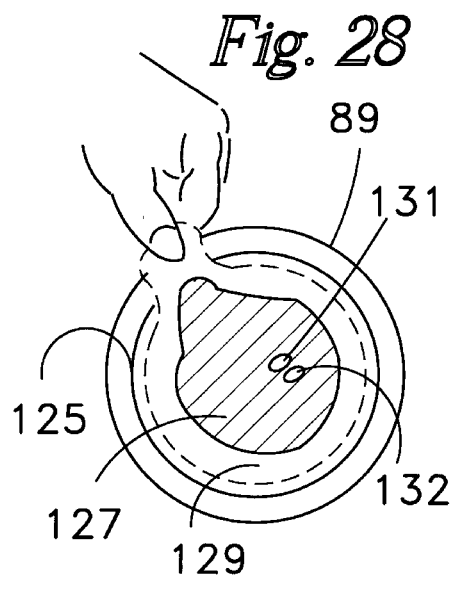
FIG. 28 illustrates the breast appliance front mold after the filler and air displacement tubes have been removed, and illustrating the rear portion of the breast appliance and the careful removal of the tapering area of the breast appliance from the breast appliance front mold.

Once the breast appliance back mold 85 is separated, a configuration similar to that shown in FIG. 28 will appear. The breast appliance 125 is visible for the first time, and particularly its back wall 127, and tapering edge 129. Two apertures 131 and 133 of the back wall 127 are visible which were formerly occupied by the tubes 103 and 105. These will be sealed will a further application of skin silicon material 111 as will be shown later.

The removal of the tapering edge 129 portion of the breast appliance 125 is of importance because of the thinness of the outer portion of the tapering edge 129. The tapering edge 129 is important to the finished product because if the edge 129 is thin enough, it can optically blend into the surrounding tissue of the client 51. Generally, the surface finish on the portion of the breast appliance 125 facing away from the client 51 while being worn will have an light scattering translucence. However, when the thinner portion is wetted and held against the skin, it becomes somewhat transparent.

Since the outer finish is not shiny this transparency, which occurs more readily at the thinner portion, provides an optical blending along a line from the client 51's natural tissue and onto the breast appliance 125. Any liquid placed between the skin of the client 51 and the tapering edge 129 will cause this optical effect. The breast appliance 125 will be mounted onto the client 51 with an application of liquid adhesive which will also serve to perform the same optical effect, even though the adhesive will "dry" or become less liquid-like as the breast appliance 125 adhered to the client 51, as will be later shown.

The thinner the radially outermost portion of the tapering edge is, the more readily will the breast appliance 125 blend into the surrounding tissues of the client. This must be balanced against the possibility of too thin a periphery which might tear upon the mounting and removal of the breast appliance 125. In any event, the tapering edge 129 will usually be difficult to removed from the rim area 95 of the breast appliance front mold 89.

It is preferred, where the removal is done by hand, to gently pull upwardly on the tapering edge 129 and to work the fingers behind and along the tapering edge 129 to gently wrest it from the rim area 95. Once the tapering edge 129 is free, along the periphery of the back wall 127 of the breast appliance 125, the breast appliance 125 may begun to be separated from the breast mold surface area 91. This too is a delicate step to be done manually since to pull the wall of the breast appliance 125 too far from the breast mold surface area 91 could cause damage. The space between the breast appliance 125 and the breast mold surface area 91 should be moved about the surface area between these two structures, working toward the nipple mold area 93.

Another method for removing the breast appliance 125 from the breast appliance front mold 89, may involve the use of compressed air. It may be forced into the area between the breast appliance 125 and the breast mold surface area 91. Going back a step, compressed air may be introduced into the holes 99 and 101 to first separate the breast appliance back mold 85 from the breast appliance front mold 89 and the skin silicone material 111 immediately adjacent the breast appliance back mold 85. Regardless of whether or not air is initially used to separate bulk areas of material from the breast appliance mold 119, care must always be taken to make sure that no one area of the set skin silicone material 111 is adhered to the inner portion of the breast appliance mold 119 so as to cause a tearing of the breast appliance.

Further, a pin hole may be formed in the breast appliance front mold at the center of the nipple mold area 93 where a small flow of compressed air may be applied to aid in separation. Other strategically placed pinholes could be arranged to introduce a higher flow of compressed air which could facilitate the removal of the breast appliance 125 from the breast appliance mold 119 in a quick and efficient manner.

Figure 29:
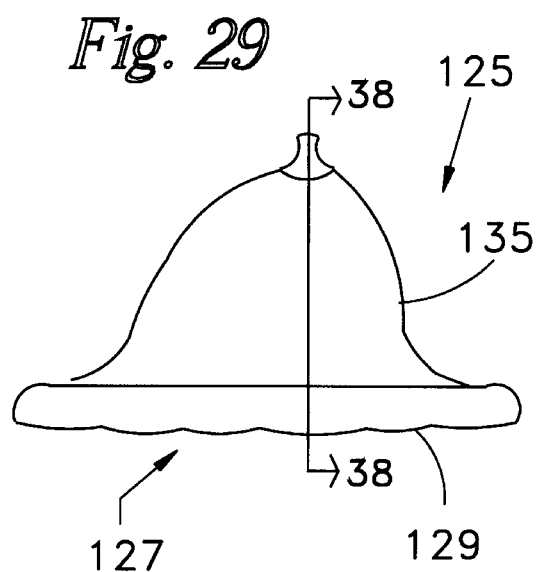
FIG. 29 illustrates the removed breast appliance.

Once the breast appliance 125 is freed from the breast appliance front mold 89, it may be turned upwardly for close inspection, as is shown in FIG. 29. In this orientation, a breast surface area 135 can be seen continuous with the tapering edge 129. The nipple surface area 137 is also visible. The outer areas of the breast appliance are inspected to detect any problems associated with the molding process, such as bubbles in the outer surface, tears, or other anomalies.

The ragged portions of the tapering edge 129 can be trimmed carefully with scissors to make certain that the breast appliance outer periphery has a smooth outer continuity. It should be remembered that too close trimming will defeat the ability of this tapering edge 129 to blend in with the skin of the client 51 once the breast appliance is mounted. It is understood that the breast appliance 125 need not always be adhesively mounted onto the chest of the client 51, but that it may be worn loosely adjacent the surgical area with a bra. This is especially where due consideration is given to the shape of the breast appliance with regard to the client 51's bra and cup size is taken to account.

Figure 30:
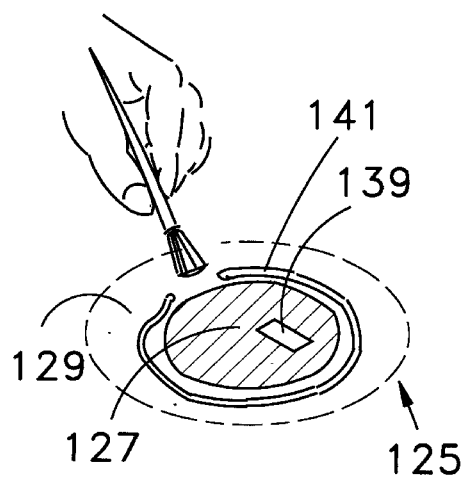
FIG. 30 illustrates application of a body adhesive to the rear of the breast appliance, and showing the sealed area where the filler tubes extended into the breast appliance.

Referring to FIG. 30, a view of the back wall 127 of the breast appliance is shown, and which illustrates a tapering edge 129 which has been trimmed and which ideally has a somewhat uniform radial dimension. The apertures 131 and 133 have been covered with an identifying label 139 which may be used to distinguish between owners, manufacturers, type of gel 117 fill, and other identifying information. The material which may be used to perform this sealing is commercially available from Dow Corning Corporation and sold under the name SILASTIC medical adhesive, type A, and identified with the catalog number 891. This adhesive is specifically intended for bonding silastic elastomers. The label 139 is then painted over with a small amount of skin silicone material 111, and allowed to set. This then seals the gel 117 within the breast appliance 125.

Figure 31:
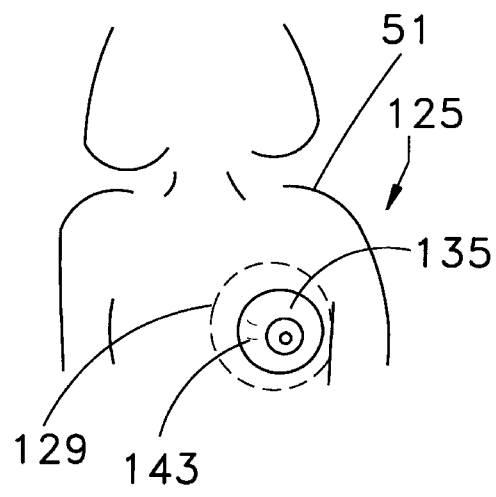
FIG. 31 illustrates the breast appliance mounted on the client and showing the outer extent of the breast appliance in dashed line format.

FIG. 30 also shows an amount of liquid adhesive 141 being brushably applied to the back side of the tapering edge 129 in anticipation of mounting of the breast appliance 129 onto the client 51. The adhesive preferred is commercially available from Dow Corning as a medical adhesive No. 355 and commercially known under the name SECURE ADHESIVE. The adhesive is preferably laid down in an elongate continuous bead. One such adhesive which has proven effective is commercially available from Referring to FIG. 31, and once the adhesive 141 has been applied along the total length of the tapering edge 129, the breast appliance 125 is oriented properly and pressed in place on the chest of the client 51. The outer periphery of the tapering edge 129 is shown in dashed line format to indicate that the outermost periphery of the tapering edge 129 will usually not be visible unless viewed extremely closely. Although the transition between the tapering edge 129 and the breast surface area 135 is shown about the periphery of the breast appliance 125, this transition is usually more obscure and undetectable.

Details may added to the skin silicone material 111 and to the gel 117 area to further cause the breast appliance 125 to have a more natural appearance. For example, where the client 51's skin is somewhat more vein like, a length of blue flocking can be laid alongside the skin silicone material 111 before the breast appliance mold 119 is closed, before the gel 117 is introduced. Later introduction of the colored gel 117, in addition to the coloring of the skin silicone material 111 which the flocking will lie behind once the breast appliance 125 is removed, will cause a vein-like appearance to appear, shown in FIG. 31 as veins 143. The look of the veins 143 may be adjusted depending upon the diameter of the flocking and how loosely it is oriented with respect to the skin silicone material 111.

Where the client 51 has freckles, they may be "painted onto" the skin silicone material 111 in a variety of ways. There are some freckles which have a sharp definition. These freckles would be painted onto the breast mold surface area 91 prior to painting on the main layers of the skin silicon material. Freckles having a medium amount of definition between the freckle color and surrounding skin color could be formed by first applying a very thin layer of skin silicone material, followed by a hand painting in of the freckle material, followed by a final application of the skin silicone material 111. In the most obscure cases, more skin silicone material 111 is left between the breast mold surface area 91 and the applied freckle color silicone material.

Once the breast appliance 125 has been adhesively placed onto the client 51, it need not be removed more than as necessary for personal hygiene in cleaning the area of the skin covered by the breast appliance 125. When used with an adhesive, the client 51 can swim, jog, etc. without worry of displacement of the breast appliance 125.

In some instances, it may be necessary to enable air to come into contact with the scar tissue 71 for a given period after surgery. In this instance, the breast appliance 125 can still be worn daily, without the adhesive 141, and secured with a bra. In this manner, the client 51 can begin to become accustomed to again having an upper body breast weight while the tissue around the scar tissue 71 continues to heal.

The processes described thus far have been selected to illustrate the most complete set of circumstances having the most steps and opportunities for capturing a client 51's physical likenesses, where those likenesses were available pre-operatively. In other instances where less than all of the client's likenesses are available pre-operatively, the methods described herein are modifiable to still give an advantageous result.

The next instance where some modification is necessary is the instance where the client 51 has had a single mastectomy. In this instance, a single breast is available for molding. When a negative body mold 61 is made, it will contain the negative mold of the existing breast on one side and a negative mold of the post operative chest area, on the other side similar to the post operative negative body mold 73. Because breasts are not identical, and only exhibit bi-lateral symmetry, the existing breast cannot normally be used to produce a direct mold of the opposite breast. However, the nipple 63 is normally directly moldable for inclusion on the other breast.

Figure 10:
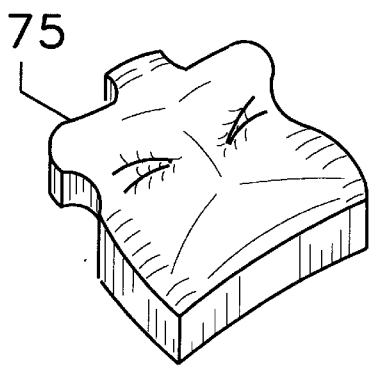
FIG. 10 illustrates the post-operative positive body mold formed from the post-operative negative mold shown in FIGS. 7–9 by the method shown in FIGS. 4 and 5, and illustrating a scar tissue area identified for further molding.

In this case, the client 51 has a post operative negative mold 75 prepared, as was shown in FIGS. 7–9, and a resulting positive body mold prepared therefrom as was shown in FIG. 10. However, the result is a positive body mold 151 as is shown in FIG. 32. The positive body mold 151 has a natural breast form 153 and a scar tissue form 155 adjacent each other. Clay can be used to sculpt a clay breast form 157, shown in FIG. 33, or clay can be pressed in an impression material and then placed on a surface for continued reshaping and sculpting.

An amount of clay is placed atop the positive body mold 151, and shaped into a form mirroring the shape of the natural breast form 153. The clay breast form 157 can then be easily lifted from the positive body mold 151 without upsetting its shape. Further, since it is sculpted and shaped while atop the scar tissue form 155, its rear end will have a shape which will fit perfectly over a breast appliance back mold 85. The sculptor can make measurements and shape comparisons upon the positive body mold 151 by using the client 51's bra. If the positive body mold 151 was taken while the client 51 was in a standing position, and if the clay breast form is made to match, the breast appliance 125 formed therefrom may not be suitable for use with a bra. In this case, a second clay breast form 157 may be desirable to make a second breast appliance which would fit more readily inside a bra. This difference is to take account of more marked differences in the position of breast as would occur with and without a bra. If the two positions are sufficiently similar, a single breast appliance 125 can serve the client 51 while wearing a bra or without. The ability to have a positive body form 151 with a natural breast form 153 for comparison greatly enhances the ability to judge these differences.

Figure 14:
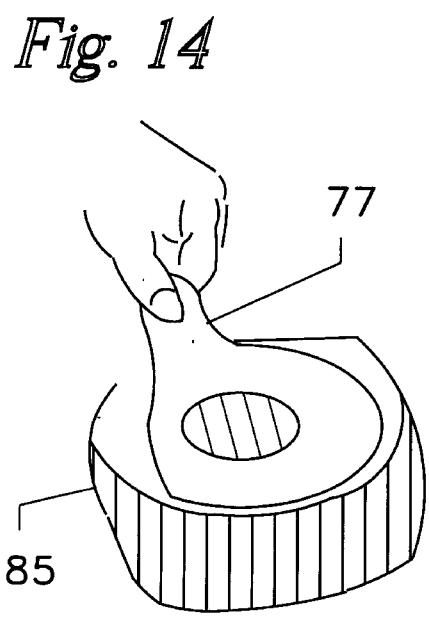
FIG. 14 illustrates the removal of the smaller alginate impression from the breast appliance back mold.

It is advisable that once the clay breast form 157 is shaped, it not be placed on a flat surface, which might obscure the shape taken from the natural breast form. It is therefore recommended that the steps shown in FIGS. 11–14 be first performed to form a breast appliance back mold 85. This will involve the formation of an alginate layer on the post operative body mold 151 rather than 75, and the formation of the breast appliance back mold 85 in a manner similar to that shown in FIGS. 12–14.

Thus, if the breast appliance back mold 85 is in position, the clay breast form 157 may be gently moved from the positive body mold 151 to the breast appliance back mold. If the clay breast form 157 is to be stored for a period of time, it is desirable to keep it moistly wrapped, as for example by a damp cloth. This will prevent shrinkage and uneven hardening.

Next, the nipple mold 67 taken as shown in FIG. 6 may be used to form a nipple. In the present case where one breast is available, the nipple mold 67 may be made from the client 51's existing breast. Although the nipple material may be made from the nipple atop the natural breast form, it should be remembered that this would produce a nipple taken from a positive plaster mold to alginate, and back to silicone. Since the client 51 is available, it is advisable to take one or several alginate negative molds of the client 51's nipple, and to then make the silicone nipples by directly painting nipple silicone material 109 into the alginate layer 53, which was shown in FIG. 6. Since virtually all of the finish errors occur from using plaster, a direct silicone on alginate mold will produce the best quality silicone nipple.

Referring to FIG. 34, a silicone nipple 159 so formed and trimmed is placed atop the clay breast form 157. In working with the clay, there is an additional advantage in that the edges of the silicone nipple 159 may be "worked" with respect to the clay to give a seamless transition from the silicone nipple 159 material to the clay material.

Where the silicone nipple 159 has a tapering edge, similar to the tapering edge 129 of the breast appliance 125, the transition from the edge of the silicone nipple 159 to the clay material of the clay breast form 157 may not need as much working to blend. Even where a small transition is left, the effects of the transition can be corrected during the inside finishing (sanding) of the breast appliance front mold 89 which will be formed.

In FIG. 34, the clay breast form 157 sits atop the breast appliance back mold 85, with the flexible barrier 81 being applied about the breast appliance back mold 85, in preparation to form the breast appliance front mold 89 as was shown in FIG. 17–19. The steps to form the breast appliance 125 are identical for the steps following FIGS. 17–19 and inclusive of FIGS. 20–31.

In a third general case, the client 51 has had surgery which has removed breast mass, but left the client 51's nipples in place. Often in this case the client 51's nipple can be extremely sensitive to touch. As such, any structure or appliance positioned to cause contact and touching movement to the client 51's nipple is to be avoided. Although the advantages from an exact fit over the client 51's chest are many from the standpoint of good fit, and movement with rather than against client 51's tissue, where the client 51's nipple is sensitive has overriding concerns. In any event, and especially where sensitivity is an issue, the range of expected motion of the client 51 which would produce undue disturbance of the nipple is not expected to be as great, and therefore the loss of close cooperation with the client 51's tissues advantageous in significant physical activity is not as important.

The breast appliance 125 formed in consideration of the sensitive nipple will have a spatial pocket formed in the rear area of the breast appliance which will fit over the client 51's nipple. Recalling the post operative mold taken with regard to FIGS. 7–9. Instead of purely scar tissue 71, there will be some scar tissue and nipple tissue present. This is shown in FIG. 35. Positive body mold 75 is now shown as having scar tissue surrounding a pair of post operative nipple shapes 161. Typically the scar tissue will extend linearly downward away from the nipple area of the breast, and often around the nipple areolar. The areas which the client 51 indicates are sensitive are noted and noted with respect to the positive body mold 75 or 151.

Once the positive body mold 75 or 151 is formed, the sensitive tissue areas are identified. An amount of clay 161 sufficient to form a pocket presenting a significant depth with respect to sensitive tissue is formed atop the nipple shapes 161 to ensure that the subsequently formed breast appliance 125 will significantly clear the client 51's nipple. By using clay applied over the positive body mold 75 or 151, several advantages can be obtained. First, using a positive material will enable ease of sculpting and can allow for the formation of a small surface area, deep pocket, or a gradually sloping volume covering a wider area.

Figure 36:
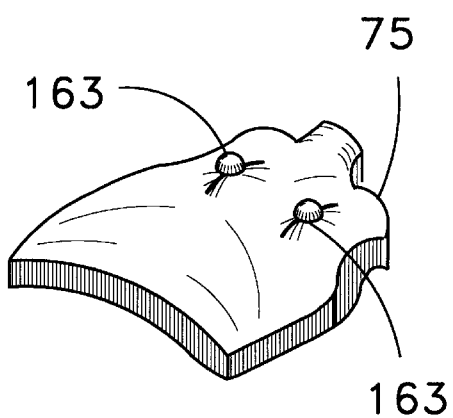
FIG. 36 illustrates the use of small clay shapes upon the sensitive nipple shapes of the positive body mold of FIG. 35 to produce a nipple clearance area in the resulting breast appliance.

Referring to FIG. 36, the use of the small amount of clay 163 on the positive body mold 75 is illustrated. The use of the clay 163 on the breast appliance back mold 85 is not advisable because there may be some problems associated with application of the skin silicone material 111 to the clay material. Also, since the breast appliance mold 119 will be closed and will be filled with the surface of the breast appliance back mold 85 oriented downward, it may be difficult to keep the small amount of clay 163 in place. In any event, it appears as if the use of the small amount of clay directly onto the positive body mold 75 is preferable.

Figure 37:
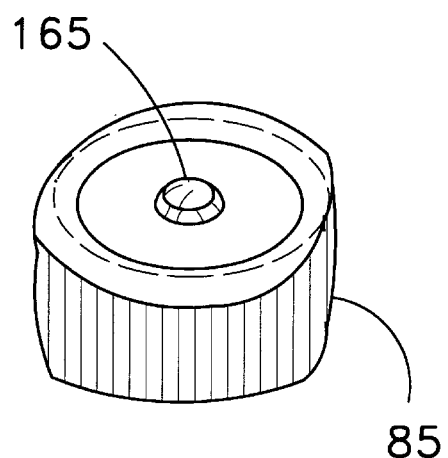
FIG. 37 illustrates a breast appliance back mold produced from the positive body mold shown in FIG. 36.

Once the small amount of clay 163 is in place, an alginate mold can be prepared from the positive body mold 75, as was shown with respect to FIGS. 10–13. This will produce a breast appliance back mold 85 having a rise 165, as is shown in FIG. 37. The breast appliance back mold 85 is then used in conjunction with a breast appliance front mold 89 to produce the breast appliance 125. Note that if a clay breast form 157 is used, and utilizing the positive body mold 75 as a support base, the small amount of clay 163 should be kept separate from incorporation into the base of the clay breast form 157 so that the clay breast form 157 will fit atop the breast appliance back mold 85 without further formation changes to accommodate the rise 165.

The next step, according to the sequences of FIGS. 15–19, would be the formation of the breast appliance 125 by pouring a plaster volume over the breast appliance back mold 85 while a clay breast form 157 is in place with respect to the breast appliance back mold 85.

Figure 38:
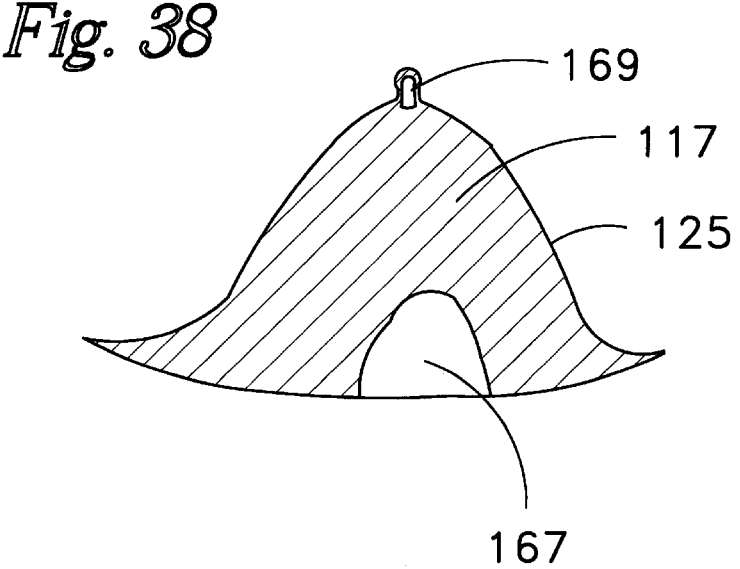
FIG. 38 is a sectional view of a breast appliance taken along line 38—38 of FIG. 29, and illustrating both a small structural air pocket for the appliance nipple, as well as the nipple pocket.

Referring to FIG. 38, a sectional view taken along line 38—38 of FIG. 26 illustrates a sectional view of a breast appliance 125 having both a nipple clearance pocket 167 and a nipple enclosed air pocket 169. The nipple enclosed air pocket 169 was formed by leaving a bubble of air within the outermost and concentrically inner most portion of the nipple mold area 93 as was discussed with regard to FIG. 24. The silicone gel 117 is visible as well.

In the fourth case, the client 51 has previously had a double mastectomy, and has neither a breast size nor shape reference. Further, the client 51 has no nipple shape reference from which to mold a nipple form. In this case, the client 51 has a post operative positive body mold 75 made, as was shown in FIGS. 7–9. From the positive body mold 75, the client 51 can direct the molding of a natural breast form of a size and shape to suit a variety of tastes.

Some considerations may include the need for a reduction in size from the client 51's previous post operative breast size. The degree of activity of the client 51 may also cause a smaller size to be of greater utility. A breast appliance 125 having a lesser depth, but wider rear surface area may be more advantageous for the active client 51.

With regard to a selection of a nipple shape and size, a nipple form can be sculpted artistically from scratch, and then molded to form a silicone nipple 159 which can then be placed atop the clay breast form 157 as was shown in FIG. 34. In the alternative, a wide array of nipple shapes will be available from previous clients 51, any one or pair of which may be selected for use, typically in the form of a silicone nipple 159.

Figure 39:
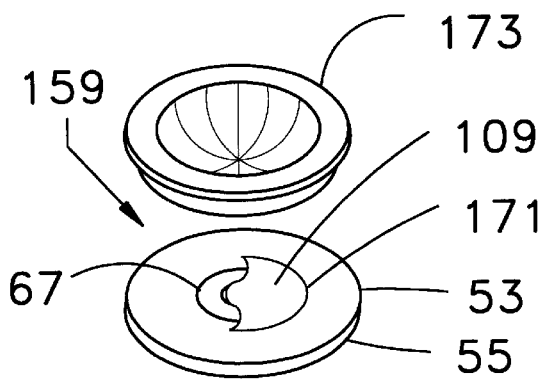

FIG. 39 illustrates the formation of a silicone nipple 159 using the small portions of the alginate material 53 supported by a small amount of plastic bandages 55. In the case of the formation of silicone nipple 159 only, it will usually not be necessary to have the rear portion of the silicone nipple 159 exactly match the client 51's area of attachment. This is because the area of attachment is relatively large compared to the mass of the silicone nipple 159.

Where the client 51 has internal implants, the use of silicone nipples 159 is quite desirable. The silicone nipples 159 are formed by pouring nipple silicone material 109 directly into the negative nipple mold 67 formed as shown in FIG. 6 to form a smooth backed surface area 171. To form a surface area 171 which matches the client 51 tissue, a mold of the client's tissue at the area where the silicone nipple 159 is to be attached can be made with alginate 53 and bandage 55 similar to that shown in FIG. 6, which will capture any details of the nipple attachment area, such as scar lines and troughs. Once a positive plaster mold 173 of the client 51 implant tissue area is made, it may be gently placed against the surface area 171 at the time the silicone nipple material 109 is poured into the nipple mold 67, as is also shown in FIG. 39.

Once the silicone nipple 159 is formed, it may be applied to the client 51's tissue using liquid adhesive 141 as was shown for the breast appliance 125, except that the liquid adhesive 141 should cover the entire surface area 171 of the silicone nipple 159.

While the present invention has been described in terms of a breast appliance and manner of making same, one skilled in the art will realize that the structure and techniques of the present invention can be applied to many situations and instances. The present invention may be applied in any situation where a prosthesis or appliance of a given consistency is to be formed.

The methods thus far discussed involve the taking of impressions directly from the skin surface of a client 51. Such direct impressions enable the replication of skin topography, including fine details of the nipple 63, areolar 65, scar tissue 71, and so on. The alginate layer 53 enables the capture of the topographical features, both post and pre-operatively to enable the breast appliance 125 to match the post operative tissues of the client 51, and to enable the frontal surfaces of the breast appliance 125 to closely approximate the client 51's own natural tissues if any were available for molding, pre-operatively.

Figure 40:
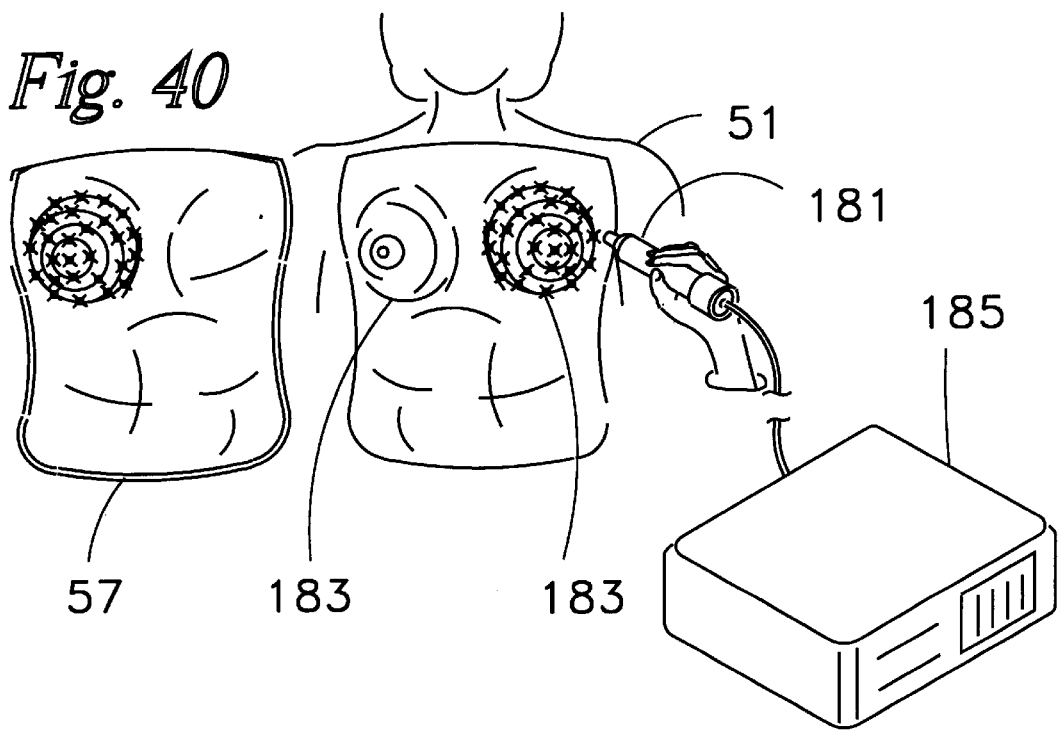
FIG. 40 illustrates the data gathering process, in lieu of a negative body mold, which can be used to generate both negative and positive body molds, as well as direct formation of a breast appliance mold.

Other methods are available for obtaining the client 51's topography and mass. Beginning at a crude level, positions on a client 51's torso can be digitized using a variety of digitization methods. Referring to FIG. 40, a client 51's chest area is digitized using a probe 181. The client's breast 183 is being digitally mapped with the probe 181. Shown is a series of data points over laid on the client's breast 183. Since naturally occurring points are to be taken, care must be had in not compressing the tissues of the client 51 to insure that a map of the topography of the client 51 is had accurately.

Further, an unlimited number of data points may be taken across the chest, neck and stomach areas to insure that a whole picture is had of the client 51's form. Using reference points of note, including the outermost tip of the nipple 63, positions on the client 51's clavicle, the client 51's navel, etc. a topological map relative to these key points can be obtained. As is shown in FIG. 40, these data points can be used to machine a negative body mold 57, or a positive body mold 61 (not shown in FIG. 40), which can then be further processed.

With the ease of taking topological data points, and the advantages of reference points of note, it is also possible to take these topological data points while the client 51 is in other positions, including bending over and lying down. These can be taken with an eye to forming a breast appliance 125 which will react more naturally. These more natural reactions may include axial elongation on bending over, frontal and downward loading on standing, and flattening out when reclining or lying down. Once points for these positions are taken, the differencing of these points will indicate the natural physical displacement of the breast 183 tissue mass. Once the natural physical displacement of the breast 183 tissue mass is known, the gel 117 within the breast appliance 125 can be cured in layers, or differentially cured to produce the corresponding natural physical displacement.

Aside from taking individual data points, other methods exist which can map the client 51's chest as a whole are known, which will enable a single scan to take an extremely high number of data points or other indicia of topography with far less effort. Further, rather than data points, vector information may be gathered to more adequately describe the chest of the client from a "sculptural" viewpoint, as will be explained.

The taking of the data points, or topographical information in this manner will eliminate the need for a negative mold 57, positive body molds, including the pre-operative positive body mold 51 and post operative positive body mold 75. In this case, the breast appliance mold 119 can be CNC or computer numerically controlled machined from any suitable material. If machined, the portions of the breast appliance mold 119 need not have a seem which is generally radial to the breast appliance 125 axis.

Further, the internal breast surface areas 91 and nipple mold areas 93 can be machine finished to any desired surface finish. Other surface details, such as freckles and moles which would be labor-intensive to add to the skin silicone material 111 can be done automatically by machine, because the size and shape and color of each freckle will be known to an extreme accuracy. Of course, further matching, and an entire pallet of colors equivalent to the client's colors would need to be generated. However, such multiple color matching and blending is simple to perform once the colors and location of the coloring are scanned into a computer 185, shown schematically in FIG. 40.

A variety of different wavelengths of light could be use to illuminate and color match the freckle type areas to insure that the colors were matched for different types of lighting and had a statistical distribution matching the client 51's skin.

Of course, if it were desired, the spatial representation of the client 51's chest area could be made into a positive body mold 61 for illustration purposes. Further, through the use of computer graphic techniques, the client 51's pre-operative torso area could be displayed on a screen, for subsequent manipulation and changing of the breast form of the client 51 before formation of the breast appliance mold 119 and breast appliance 125.

Figure 41:
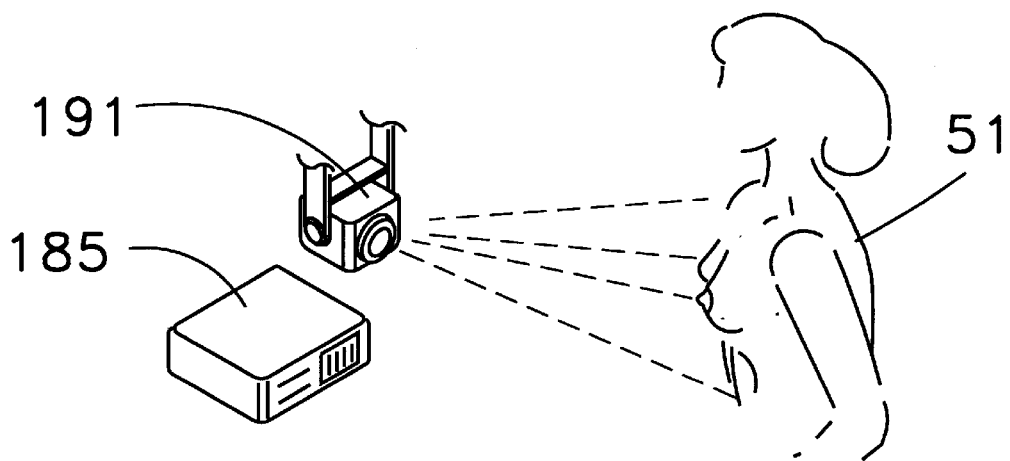
FIG. 41 illustrates the scanning in of data directly, covering all data points, with the use of a scanner.

An optical scan is shown in FIG. 41 and illustrates a scanner 191 scanning the torso and breasts 183 of the client 51, into the computer 185. A similar optical scan can be taken post-operatively and differenced with respect to the pre-operative scan. Such as technique has the advantage of defining the outermost regions, taken concentric to the client 51's breast, for which a change has occurred. This will enable the formation of a breast appliance having significant deviations from radial constancy, particularly with respect to the back wall 127 of the breast appliance 125, especially since some body forms include significant undercuts resulting from a significant overhang.

In some breast forms, there is a significant overhang of the bottom of the breast onto the lower rib cage. These can be difficult to properly mold. Often, one breast appliance 125 is provided for the standing, bra-less configuration, while another is provided for the bra-covered position. A more thorough scan of the client 51 topology, particularly in bending, standing, and lying position, will enable a breast appliance to be made which will most closely approximate the client 51's natural breast 183.

This is easier to accomplish in the case of firmer breasts and most difficult in the case of softer breasts which have extreme positional displacement on change of body position. The gel 117 mass may be allowed to cure in layers having a shape which facilitates positional displacement of the layers in a manner which will approximate the change in position and shape of a natural breast under the influence of a change in a client 51's position. One such orientation would involve the formation of gel layers using a separating, removable divider to prevent curing between the layers. This configuration is shown in FIG. 42.

This sectional view illustrates the gel 117 as divided into layers 195, each layer 195 having the ability to slide with respect to adjacent layers 195. The layers 195 may or may not be set with respect to the skin silicone material, especially the layers 195 in between the forward most and rearward most layers 195. This sliding plate action will enable the breast appliance 125 to move radially about in a more natural manner. Beyond this simplicity, the complex motions captured by the scanner 191 can enable layers 195 other than a set of parallel layers 195 to be incorporated into the breast appliance 125. The specific layering will be determined by the central amounts of tissue of the client 51, and the direction of displacement under differing gravitational influences and client 51 movement.

Figure 42:
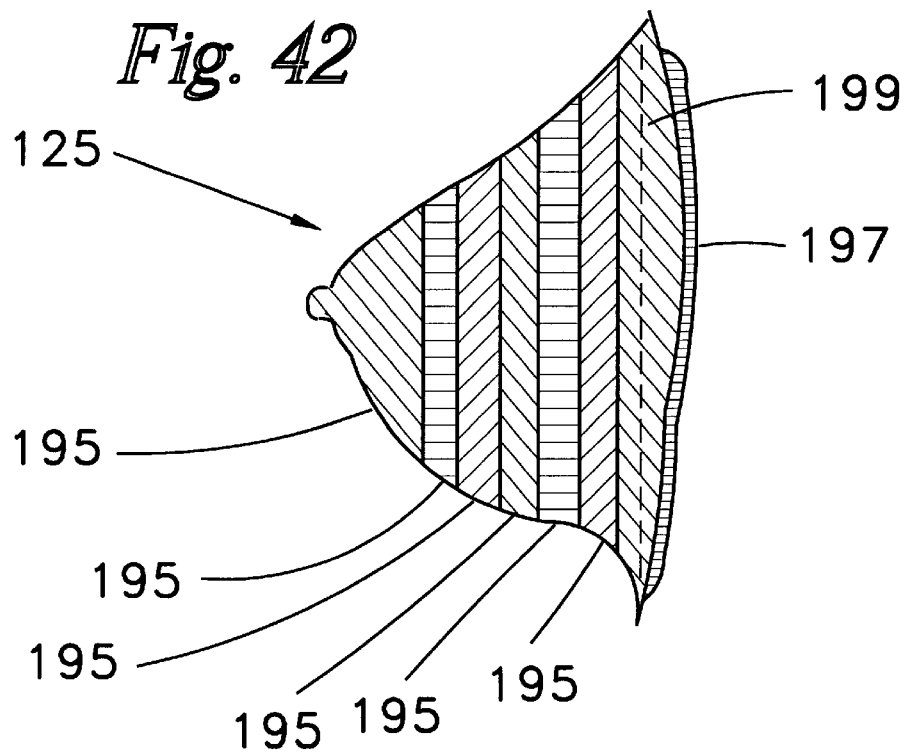
FIG. 42 is a sectional view of a breast appliance designed to have a structure to permit more natural movement and having a structure which will enable simulation of the client's pre-operative breast displacement under movement conditions.

Another option to the breast appliance 125 of all embodiments of the present invention is also shown in FIG. 42. An insulative pad 197 is includable onto the back wall 127 of the breast appliance 125. The insulative pad may be thin enough to accommodate the shape of the back wall 127 and the scar tissue 71 of the client 51 so as to not mitigate the advantage of having matched surfaces. An insulative pad is often desirable in very hot or very cold weather.

In cold weather, the relatively large surface area of the breast appliance 125 will tend to lose heat faster than the surface of the client 51's tissue to which it is attached. This can cause a cold spot on the client's chest in its area of contact with breast appliance 125, which can be uncomfortable. Similarly, excessive heat can be transmitted to the client's chest, with no opportunity for expiration and evaporative cooling. Insulative pad 197 can prevent undue cooling and undue heating provided it gives sufficient resistance.

As a further alternative, a heat resistant material could be applied to the skin silicone material 111 just after the skin silicone material is applied to the breast appliance back mold 85. Since the cured silicone gel 117 will not circulate within the breast appliance 125, an insulative pad 197, if placed within the skin silicone envelope can still function to block heat. This internally placed insulative pad 199 is shown in FIG. 42 in dashed line format.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A breast appliance for conformance to the chest surface of a wearer comprising:

a mass of partially cured silicone;

a layer of skin silicone material enveloping and cured with and to said mass of partially cured silicone, such that said mass of partially cured silicone will not separate from said layer of skin silicone, a portion of said layer of skin silicone material having a back wall molded to conform to an impression taken from the chest of the wearer, said back wall having a tapering edge about the periphery of said back wall to assist in blending said breast appliance into an area of surrounding skin of said wearer, said skin silicone material having a front portion continuous with said tapering edge of said back wall and having a first shade of color additive dispersed within a volume of material of said skin portion of said front portion, and having a second shade of color additive different than said first shade of color additive dispersed within a volume of material of a nipple portion of said front portion of said skin silicone material, said nipple portion continuous with and cured to said skin portion and having a greater hardness than said skin portion of said front portion of the layer of skin silicone material and; wherein a third shade of color additive is dispersed throughout said mass of partially cured silicone; and wherein said first and said second and said third shades of color additive are a face powder dispersion color additive and form a suspension having color and depth tones comparable with a surface color and a depth of skin tone of said wearer.

2. The breast appliance recited in claim 1 wherein said breast appliance is made for fitting over a post operative surgical area of said wearer resulting from removal of a breast of said wearer and wherein said front portion, including said skin portion and said nipple portion of said layer of skin silicone material has an outward surface topography physically measured from an outward topography of said breast of said wearer.

3. The breast appliance recited in claim 2 wherein said layer of skin silicone material of said back wall has an outward surface topography physically measured from a post surgical area outward topography of said wearer.

\* \* \* \* \*